United States Patent
Imangholi

(10) Patent No.: US 11,696,812 B2
(45) Date of Patent: Jul. 11, 2023

(54) LIGHTING ELEMENT

(71) Applicant: Invuity, Inc., San Francisco, CA (US)

(72) Inventor: Babak Imangholi, Oakland, CA (US)

(73) Assignee: Invuity, Inc., San Francisco, CA (US)

( * ) Notice: Subject to any disclaimer, the term of this patent is extended or adjusted under 35 U.S.C. 154(b) by 960 days.

(21) Appl. No.: 16/468,812

(22) PCT Filed: Oct. 23, 2017

(86) PCT No.: PCT/US2017/057808
§ 371 (c)(1),
(2) Date: Jun. 12, 2019

(87) PCT Pub. No.: WO2018/080963
PCT Pub. Date: May 3, 2018

(65) Prior Publication Data
US 2020/0078132 A1     Mar. 12, 2020

Related U.S. Application Data

(60) Provisional application No. 62/412,195, filed on Oct. 24, 2016.

(51) Int. Cl.
*A61B 90/35* (2016.01)
*H01L 33/62* (2010.01)
(Continued)

(52) U.S. Cl.
CPC ............. *A61B 90/35* (2016.02); *H01L 33/62* (2013.01); *A61B 17/3211* (2013.01);
(Continued)

(58) Field of Classification Search
CPC . A61B 90/35; A61B 17/3211; A61B 18/1402; A61B 2090/306;
(Continued)

(56) References Cited

U.S. PATENT DOCUMENTS

| | | | |
|---|---|---|---|
| 1,639,996 A | * | 8/1927 | Groff ................. A61B 18/1402 |
| | | | 30/337 |
| 4,322,735 A | | 3/1982 | Sadamasa et al. |

(Continued)

FOREIGN PATENT DOCUMENTS

| | | |
|---|---|---|
| CN | 204611395 U | 9/2015 |
| CN | 105280616 A | 1/2016 |

(Continued)

OTHER PUBLICATIONS

English Translation of Abstract of Chinese Patent Application No. 105280616 dated Feb. 9, 2021.

(Continued)

*Primary Examiner* — Tsion Tumebo
(74) *Attorney, Agent, or Firm* — McDonnell Boehnen Hulbert & Berghoff LLP

(57) ABSTRACT

Surgical lighting must balance various needs of a user: the light must be bright, but not too thermally hot; directed at a target, but not shining elsewhere; be robust, yet compact. Often much of these myriad needs must be accomplished by ever small illumination elements placed into devices requiring ever lower profiles. However, current surgical illumination options require the use of bulky lighting elements if the desire target is to be illuminated or, conversely, use weaker lighting elements for sleeker designs.

23 Claims, 15 Drawing Sheets

(51) Int. Cl.
  *A61B 90/30* (2016.01)
  *A61B 17/3211* (2006.01)
  *A61B 18/14* (2006.01)
(52) U.S. Cl.
  CPC ..... *A61B 18/1402* (2013.01); *A61B 2090/306* (2016.02); *A61B 2090/309* (2016.02); *H01L 2933/0066* (2013.01)
(58) Field of Classification Search
  CPC .... A61B 2090/309; A61B 2018/00095; A61B 2018/00601; A61B 2018/1412; A61B 90/30; H01L 33/62; H01L 2933/0066
  See application file for complete search history.

(56) References Cited

U.S. PATENT DOCUMENTS

| | | | | |
|---|---|---|---|---|
| 4,754,754 | A * | 7/1988 | Garito | A61B 17/3213 606/49 |
| 5,800,427 | A * | 9/1998 | Zamba | A61B 18/1402 606/39 |
| 5,814,871 | A * | 9/1998 | Furukawa | H01L 31/02325 257/E31.127 |
| 5,863,406 | A * | 1/1999 | Mazzoni | H05K 3/3473 29/840 |
| 6,610,057 | B1 | 8/2003 | Ellman et al. | |
| 8,317,693 | B2 * | 11/2012 | Grey | A61B 1/267 600/199 |
| 8,636,733 | B2 * | 1/2014 | Heard | A61B 18/1477 606/42 |
| 8,866,169 | B2 | 10/2014 | Emerson et al. | |
| 9,041,229 | B1 * | 5/2015 | Johnson | H01L 24/81 257/E23.021 |
| 9,496,170 | B2 | 11/2016 | Yang et al. | |
| 9,825,016 | B1 * | 11/2017 | Kim | H01L 27/124 |
| 2004/0245591 | A1 * | 12/2004 | Wang | H01L 25/0753 257/E25.02 |
| 2005/0117356 | A1 | 6/2005 | Lin | |
| 2006/0231853 | A1 | 10/2006 | Tanaka et al. | |
| 2007/0111500 | A1 | 5/2007 | Cowens et al. | |
| 2007/0262328 | A1 | 11/2007 | Bando | |
| 2010/0252851 | A1 | 10/2010 | Emerson et al. | |
| 2012/0099321 | A1 | 4/2012 | Scott et al. | |
| 2015/0002023 | A1 * | 1/2015 | Imangholi | H01L 33/32 315/129 |
| 2015/0021629 | A1 | 1/2015 | Gershowtiz et al. | |
| 2016/0014878 | A1 | 1/2016 | Kilhenny | |
| 2016/0020176 | A1 | 1/2016 | Yang et al. | |
| 2016/0131352 | A1 | 5/2016 | Thirunavukarasu et al. | |
| 2016/0157920 | A1 | 6/2016 | Vayser et al. | |
| 2019/0015147 | A1 * | 1/2019 | Hubelbank | A61B 18/1402 |

FOREIGN PATENT DOCUMENTS

| | | |
|---|---|---|
| JP | 2001036154 A | 2/2001 |
| JP | 2006-278511 A | 10/2006 |
| JP | 2007180591 A | 7/2007 |

OTHER PUBLICATIONS

Int'l Search Report and Written Opinion for PCT/US2017/057808, dated Jan. 2, 2018 (9 pages).

English Abstract of Japanese Patent Application No. 2001-036154 dated Oct. 6, 2021.

English Abstract of Japanese Patent Application No. 2007-180591 dated Oct. 6, 2021.

* cited by examiner

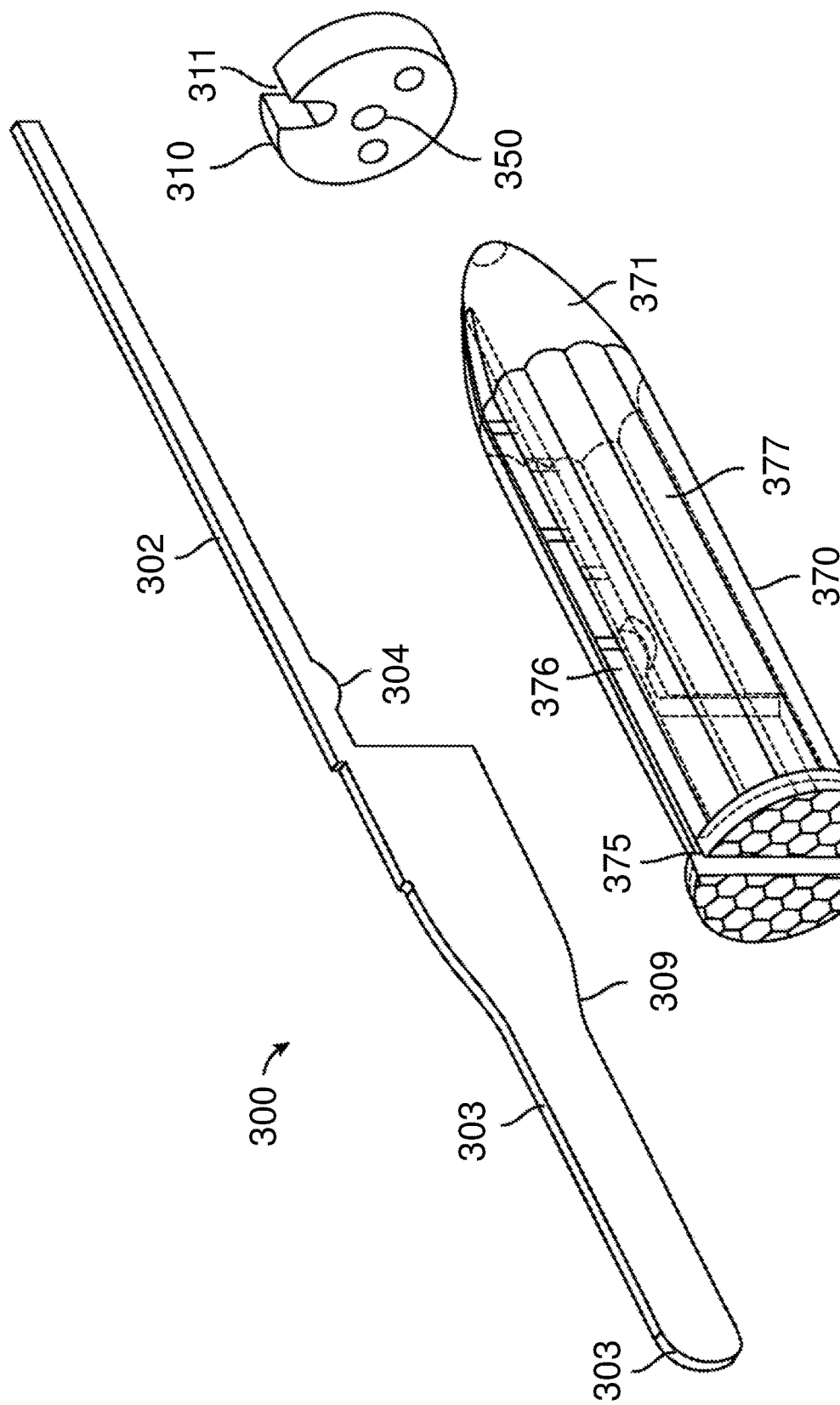

SECTION B-B

LIGHTING ELEMENT

CROSS-REFERENCE

This application is a national phase under 35 U.S.C. § 371 of International Application No. PCT/US17/57808, filed Oct. 23, 2017, which claims the benefit of priority to U.S. Provisional Patent Application No. 62/412,195, filed Oct. 24, 2016, the contents of which are incorporated herein by reference in their entirety.

BACKGROUND OF THE INVENTION

1. Field of the Invention

Surgical lighting must balance various needs of a user: the light source must be bright, but not generate too much heat; directed at a target, but not shining elsewhere; be robust, yet compact so they do not obstruct access to the surgical field. Often much of these myriad needs must be accomplished by ever small illumination elements placed into devices requiring ever lower profiles. However, most current surgical illumination options require the use of bulky lighting elements if the desired target is to be illuminated or, conversely, use weaker lighting elements for sleeker designs.

2. Background Art

Myriad light emitting devices, systems, and methods have been developed over the years such as: U.S. Pat. No. 7,052,152 (to Harbers and Collins, assigned to Philips Lumileds Light Company, LCC) entitled "LCD BACKLIGHT USING TWO-DIMENSIONAL ARRAY LEDS;" U.S. Pat. No. 7,824,070 (to Higley, Chen, and Coleman, assigned to Cree, Inc.) entitled "LED LIGHTING FIXTURE,"
U.S. Pat. No. 8,022,626 (to Hamby, Scotch, and Selverian, assigned to Osram Sylvania Inc.) entitled "LIGHTING MODULE;" U.S. Pat. No. 8,895,998 (to Hussell et al., assigned to Cree, Inc.) entitled "CERAMIC-BASED LIGHT EMITTING DIODE (LED) DEVICES, COMPONENTS AND METHODS;" U.S. Pat. No. 8,916,896 (to Andrews and Adams) assigned to CREE, Inc.) entitled "LIGHT EMITTER COMPONENTS AND METHODS HAVING IMPROVED PERFORMANCE;" U.S. Pat. No. 9,212,808 (to Higley, Chen, and Coleman, assigned to Cree, Inc.) entitled "LED LIGHTING FIXTURE;" U.S. patent application Ser. No. 12/248,841 (to MacNeish et al.) entitled "CERAMIC EMITTER SUBSTRATE;" U.S. patent application Ser. No. 13/327,219 (to Helbing, assigned to Bridgelux, Inc.) entitled "EFFICIENT LED ARRAY;" U.S. patent application Ser. No. 14/217,701 (to Ishizaki et al., assigned to Sharp Kabushiki Kaisha) entitled "LIGHT EMITTING DEVICE;" U.S. patent application Ser. No. 14/168,561 (to Tudorica et al., assigned to CREE, Inc.) entitled "LIGHT EMITTER DEVICES AND METHODS FOR LIGHT EMITTING DIODE CHIPS;" and U.S. patent application Ser. No. 15/067,145 (to West et al., assigned to Bridgelux, Inc.) entitled "PACKAGING A SUBSTRATE WITH AN LED INTO AN INTERCONNECT STRUCTURE ONLY THROUGH TOP SIDE LANDING PADS ON THE SUBSTRATE."

SUMMARY OF THE INVENTION

Recognizing the need to improve light—by reducing profile while maintaining intensity—the present disclosure generally relates to improved light elements, methods of their use, and methods of their manufacture. More specifically, the present disclosure relates to improved surgical lighting within the context of devices, systems, and methods of surgical illumination.

In an aspect of the present disclosure, a light emitting device for illuminating a surgical target comprises a base, a conductive layer (with at least a portion of the conductive layer coupled to the top of the base), an insulating layer (with at least a first portion of the insulating layer coupled to the top of the the conductive layer and a second portion of the insulating layer coupled to the top of the base, and a light emitter, wherein one or more holes, sized to receive a conductor element, extend through the base, the conductive layer, and the insulating layer. The light emitting device may further comprise at least one conductor element that extends through at least one hole extending through the base, the conductive layer, and the insulating layer, and the at least one conductor element is electrically coupled with the light emitter. The at least one conductor element may be in electrical contact with the conductive layer either through a conductive surface or a conductive edge or both. Electrical coupling of at least one conductor element and the conductive layer may be facilitated through a conductive medium, such as solder.

In another aspect of the present disclosure, a light emitting system for illuminating a surgical target comprises a surgical device with a proximal portion and a distal portion and a light emitting device disposed within the distal portion of the surgical device. The light emitting device may comprise a base, a conductive layer (with at least a portion of the conductive layer is coupled atop the base), an insulating layer (with at least a first portion of the insulating layer coupled atop the conductive layer and a second portion of the insulating layer coupled atop the base), and a light emitter, wherein one or more holes, sized to receive a conductor element, extend through the base, the conductive layer, and insulating layer. The surgical device may comprise a scalpel or an electrode. Optionally, the light emitting system may further comprise at least one conductor element that extends through at least one hole extending through the base, the conductive layer, and the insulating layer, and the at least one conductor element is electrically coupled with the light emitter. The at least one conductor element may be in electrical contact with the conductive layer either through a conductive surface or a conductive edge or both. Electrical coupling of at least one conductor element and the conductive layer may be facilitated through a conductive medium, such as solder.

In another aspect of the present disclosure, a method of manufacturing a light emitting device comprises applying solder to a substrate package, placing one or more conductor elements into one or more conductor element receiving holes of the substrate package, each of the one or more conductor elements having a top and a bottom, reflowing solder applied to the substrate package, affixing the substrate package into a machine to remove excess material from the one or more conductor elements, removing the excess material from the one or more conductor elements, applying one or more light emitters to the substrate package, and reflowing solder applied to the substrate package. The one or more conductive elements may comprise a pin or wire. Optionally, the substrate package may comprise a base, a conductive layer, and an insulating layer. In some instances, at least on conductor element may be put in electrical contact with the conductive layer. Optionally, said affixing the substrate package may comprise clamping the substrate package along an overlapping portion of the base into a grinding machine. In some instances, said removing may comprise grinding, milling, laser machining such that a top of the one or more conductor elements is about level with the insulating layer. In some instances, said reflowing may comprise establishing electrical contact between the light emitters and the one or more conductor elements or the conductive layer. Optionally, said reflowing solder may comprise placing the substrate into a reflow oven.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3C shows an exploded view of FIG. 3B.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1A:
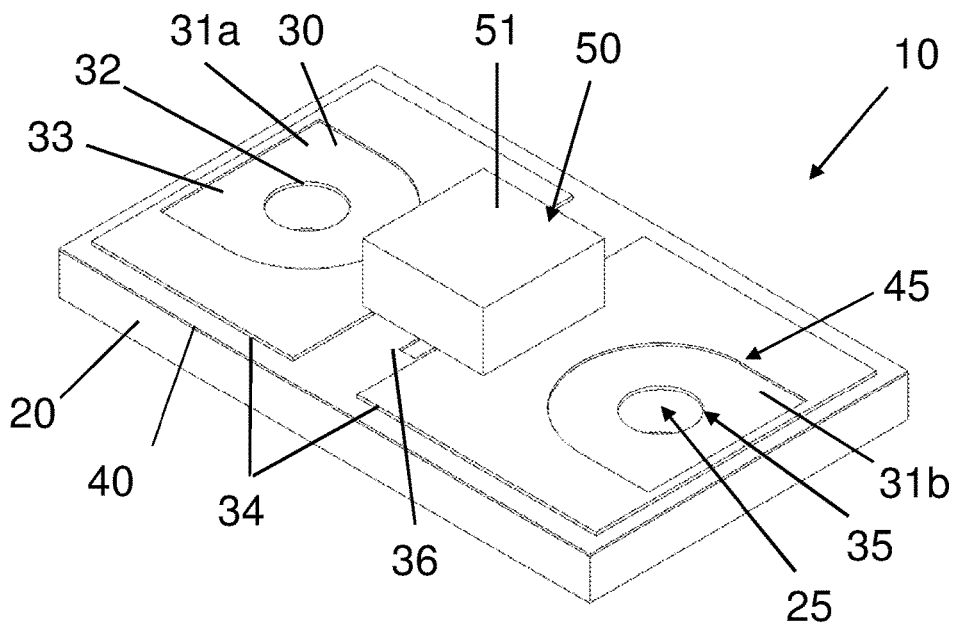
FIGS. 1A-1B show an exemplary embodiment of a light emitting device with a single light emitter.
Figures 1B, 1C:
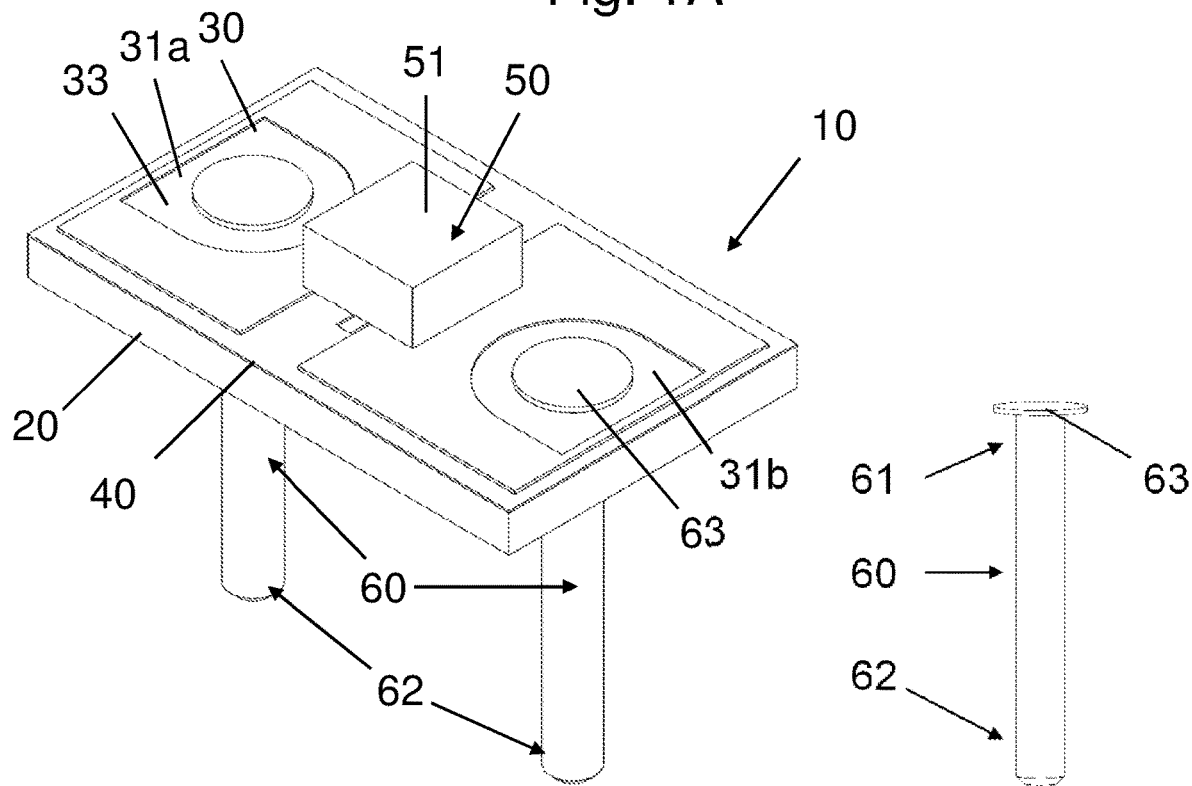
FIG. 1C shows a pin that may couple to the light emitting device.

FIGS. 1A-1B show an exemplary embodiment of a light emitting device 10 comprising a base 20, a conductive layer 30, an insulating layer 40, and a single light emitter 50.

The base 20 of this or any embodiment disclosed herein may have a posterior surface and an anterior surface. When describing the base 20 or any other layer (e.g., the conductive layer 30, the insulating layer 40, etc.) herein the terms "bottom surface" and "top surface" may also be used to refer to the posterior surface and anterior surface, respectively. Atop the anterior surface of the base 20 may be a conductive layer 30, an insulating layer 40, or a combination of a conductive layer 30 and an insulating layer 40. The conductive layer 30 and/or insulating layer 40 may be coupled, bonded, adhered, soldered, or otherwise in physical, operative, and/or thermal contact with the base 20 in any combination. For example, in some embodiments, the conductive layer 30 may extend over at least a portion of the top surface of the base 20. In some embodiments, the conductive layer 30 may extend over at least a first portion of the top surface of the base 20 and the insulating layer 40 may extend over at least a second portion of the top surface, where the first portion of the top surface and the second portion of the top surface do not intersect (and therefore, the conductive layer 30 and the insulating layer 40 do not overlap). In other embodiments, the conductive layer 30 may extend over at least a first portion of the top surface of the base 20 and the insulating layer 40 may extend over at least a second portion of the top surface of the base 20, wherein the first portion of the top surface and the second portion of the top surface will intersect (e.g., a first subset of the first portion of the top surface and a second subset of the second portion of the top surface will correspond). For such embodiments, the insulating layer 40 may overlap (e.g., lay atop) the conductive layer 30 or the conductive layer 30 may overlap (e.g., lay atop) the insulating layer 40. The first portion of the top surface and the second portion of the top surface may partially and/or completely overlapping. In some embodiments, the insulating layer 40 may partially or completely overlap the conductive layer 30. These and other embodiments representing the overlap of a first layer (e.g. a conductive layer 30) and a second layer (e.g., an insulating layer 40) on a substrate (e.g., a base 20) can be seen illustrated in FIGS. 9A-9H.

In some embodiments, a portion of the anterior surface of the base 20 may be coupled to the conductive layer 30 and a portion of the anterior surface of base 20 may be coupled to the insulting layer 40. Alternatively or in combination with any embodiment described herein, a portion of the anterior surface of the base 20 may not be covered or coupled to any layer.

The base 20 of this or any embodiment may comprise one or more thermally conductive and electrically non-conductive materials (e.g., in composite form, as an alloy, etc.) so that heat may be transferred without risk of electrically shorting any portion of the light emitting device 10. Such thermally conductive and electrically non-conductive materials include but are not limited to alumina (e.g., $Al_2O_3$), aluminum nitride, aluminum oxide, aluminum oxide ceramic substrate, boron nitride, boron nitride powder, ceramic, corundum cubic boron nitride (such as Borazon®), gas pressure sintered silicon nitride, high strength substrate alumina, hot-pressed aluminum nitride, hot-pressed boron nitride, hot-pressed silicon nitride, microplasmic anodizing ceramic coatings (e.g., for aluminum, magnesium, titanium, zirconium, etc.), pyrolytic boron nitride, silicon nitride (e.g., $Si_3N_4$, $Si_3N_4$—$Y_2O_3$, etc.), sintered alumina, sintered reaction bonded silicon nitride, zirconia, zirconia toughened alumina. Other possible materials that may comprise the base 20 as an alternative to or in combination with any of the aforementioned materials for the base 20 include aluminum, gold, silver, cobalt, chromium, copper, iron, magnesium, nickel, lead, platinum, steel, titanium, tin, silicon, tungsten, and zinc. Preferably the base 20 is comprised of at least one material with a thermal conductivity greater than about 20 W/m-K. Preferably the base 20 is comprised of at least one material with an electrical resistivity greater than about $10^{10}$ ohm-cm. Even more preferably the base 20 is comprised of at least one material with a thermal conductivity greater than about 20 W/m-K and an electrical resistivity greater than about $10^{10}$ ohm-cm. The base 20 may comprise aluminum nitride or a comparable ceramic.

The base 20 of this or any embodiment may comprise one or more holes 25. The illustrated examples of FIGS. 1A-1B show two holes that extend through the entirety of the thickness. The holes 25 in the base 20 may be created via any method known in the art including but not limited to drilling, electrical discharge machining, laser machine, milling, punching, etc. Though illustrated here and elsewhere as circles, the holes 25 of the base 20 may take on any shape including an ellipse, an oval, a semi-circle, a square, etc.

The conductive layer 30 of this or any embodiment may comprise one or more conductive pads. In the illustrated example, two conductive pads 31a, 31b are shown, each having a posterior surface, a portion of which is coupled to at least a portion of the anterior surface of the base 20, and an anterior surface. The conductive pads 31a, 31b may have a first conducting surface, herein referred to as a conductive edge 32—a surface through which electricity (e.g., current, potential, etc.) may pass. The conductive edge 32 may be in physical and/or electrical contact with a conductor element such as a pin or wire (for example, as seen in FIG. 1B) such that at least some portion of the available electricity is able to pass through at least some portion of the conductive edge 32. Alternatively or in combination, the conductive pads 31a, 31b may have a second conducting surface, herein referred to as a conductive surface 33. The conductive surface 33 may be in physical and/or electrical contact with a conductor element such as a pin or wire (for example, as seen in FIG. 1B) such that at least some portion of the available electricity is able to pass through at least some portion of the conductive surface 33. The use of the terms "first" and "second" are for reference purposes and are not intended to suggest that one has priority over the other in this or any embodiment. For instance, some embodiments use a conductive edge 32 exclusively, while other embodiments use a conductive surface 33 exclusively. Some embodiments may comprise both a conductive edge 32 and a conductive surface 33. The conductive pads 31a, 31b may be separated by a gap 36 between them so that they are not in electrical contact.

The conductive layer 30 of this or any embodiment may comprise one or more electrically conductive materials (e.g., in composite form, as an alloy, etc.). Such electrically conductive materials include but are not limited to aluminum, brass, bronze, carbon, carbon steel, copper, gold, iron, lead, lithium, mercury, molybdenum, nickel, palladium, platinum, silver, stainless steel, tin, titanium tungsten, and zinc.

The conductive layer 30 of this or any embodiment may have an extension 34 extending beyond the base 20. The extension 30 may be about equal to the thickness of the conductive pads 31a, 31b or about equal to the sum of the thickness of the conductive pads 31a, 31b and the thickness of the insulating layer 40. In some embodiments, the base 20 may comprise an offset, notch, groove, and/or dwelling to inlay the conductive layer 30 and/or one or more of the conductive pads 31a, 31b so that the outer surface remains flush or essentially flush. In some embodiments, the base 20 may comprise an offset, notch, groove, and/or dwelling to inlay the conductive layer 30 and/or one or more of the conductive pads 31a, 31b such that the extension 34 of the conductive layer 30 may remain flush or essentially flush with the base 20. In some embodiments, the base 20 may comprise an offset, notch, groove, and/or dwelling to inlay the conductive layer 30 and/or one or more of the conductive pads 31a, 31b such that the extension 34 of the conductive layer 30 may remain flush or essentially flush with the anterior surface of the base 20.

The conductive layer 30 of this or any embodiment may comprise one or more holes 35. The illustrated examples of FIGS. 1A-1B show two holes that extend entirely through the thickness of the conductive layer 30. In some embodiments the conductive pads 31a, 31b may each comprise one or more holes 35. The holes 35 in the conductive layer 30 may extend at least partially through the thickness of the conductive layer 30. The holes 35 of the conductive layer 30 may substantially align with the holes 25 of the base 20. The holes 35 in the conductive layer 30 may be created via any method known in the art including but not limited to drilling, electrical discharge machining, laser machine, milling, etc. The holes 35 of the conductive layer 30 may be created independently of the holes 25 of the base 20. The holes of the conductive layer 30 may be created simultaneously as the holes 25 of the base 20. Though illustrated here and elsewhere as circles, the holes 35 of the conductive layer 30 may take on any shape including an ellipse, an oval, a semi-circle, a square, etc. The holes 35 of the conductive layer 30 may be substantially the same shape as the holes 25 of the base 20. Conversely, the shape of the holes 35 of the conductive layer 30 may be independent and/or different from the shape of the holes 25 of the base 20. The size of holes 35 of the conductive layer 30 may be less than, about equal to, or greater than the size of the holes 25 of the base 20.

There may be one or more passageways corresponding to one or more channels demarcated by the combination of one or more holes in both the base 20 and the conductive layer 30. Each of the one or more passageways may have a perimeter that is approximately the same size and shape as the perimeter of a conductor element that spans across the passageway.

At least a portion of the insulating layer 40 of this or any embodiment may be coupled atop the base 20, the conductive layer 30, the conductive pads 31a, 31b, or any combination thereof.

The insulating layer 40 may comprise any solder mask known in the art. The insulating layer may be deposited via screen print (with, for example, an ultraviolet or thermal curing mechanism), coating, curtain coating, electrostatic spray, high volume low pressure (HVLP) air spray, ink jet, laser direct imaging, as a liquid photoimageable solder mask, or as a dry mask.

The insulating layer 40 of this or any embodiment may comprise one or more holes 45 preferably aligned with the holes of the layers underneath. The illustrated examples of FIGS. 1A-1B show two holes that extend entirely through the thickness of the insulating layer 40. The holes 45 may either made before and/or during an initial formulation of the insulating layer 40 or they may be created after the insulating layer 40 has been made. For those embodiments comprising holes 45 made before and/or during the initial formulation of the insulating layer 40, the holes 45 may be generated through initial ceramic shaping in a furnace, sintering, hot pressing, hot isostatic pressing, chemical vapor deposition, and/or reaction bonding. For those embodiments comprising holes 45 made after the initial formulation of the insulating layer 40, the holes 45 may be created using mechanical drilling (e.g., with a diamond coated drill), through electron beam drilling, ion beam drilling, or plasma drilling. Holes 45, either individually or collectively, may be create via laser cutting (e.g., by a carbon dioxide ($CO_2$) laser, a neodymium (Nd) laser, a yttrium-aluminum-garnet (YAG) laser, an Nd-YAG laser, etc.). Photolithographic techniques may also be used to create the holes 45 of this or any embodiment. The holes 45 may be made via any method known in the art. The holes 45 of the insulating layer 40 may be created independently of the holes 25 of the base, of the holes 35 of the conductive layer 30, or both. The holes of the insulating layer 40 may be created simultaneously as the holes 25 of the base 20, the holes 35 of the conductive layer 30, or both. Though illustrated here with a D-shape (that is, approximately about half of a circle and half of a square), the holes 45 of the insulating layer 40 may take on any shape including an ellipse, an oval, a semi-circle, a square, etc. The holes 45 of the insulating layer 40 may be substantially the same shape as the holes 25 of the base 20, the holes 35 of the conductive layer 30, or both. Conversely, the shape of the holes 45 of the insulating layer 40 may be independent and/or different from the shape of the holes 25 of the base 20, the holes 35 of the conductive layer 30, or both. The size of holes 45 of the insulating layer 40 may be less than, about equal to, or greater than the size of the holes 25 of the base 20 and/or the size of the holes 45 of the insulating layer 40 may be less than, about equal to, or greater than the size of the holes 35 of the conductive layer 30. The illustrated embodiment shows the holes 45 of the insulating layer 40 larger than that the holes 35 of the conductive layer 30 leaving an exposed region of the conductive layer 30 (in this case, an exposed region on each of the conductive pads 31a, 31b). The exposed region of the conductive layer 30 may comprise a conductive surface 33. The exposed region of the conductive layer 30 may provide a region on which a conductor element such as a pin or a wire may be in physical and/or electrical contact with the conductive layer 30. The exposed region of the conductive layer 30 may provide a region on which solder or other physical or electrical connective media may be used to couple the conductive layer 30 to a conductor element (such as a pin, wire, or other electrical connection) and/or one or more structural elements. The conductor element may be coupled to the conductive layer via a conductive adhesive, crimp connections, one or more terminal blocks, posts, one or more plug and socket connections, a blade connection, a ring and spade terminal, splicing the conductor element into or around the conductive layer, splicing the conductive layer into or around the conductor element, etc.

The insulating layer 40 of this or any embodiment may comprise holes (not shown) that permit at least a portion of the light emitter 50 to contact (e.g., physically, electrically, thermally, etc.) at least a portion of the conductive layer 30, the base 20, or both. For example, light emitter 50 may have a first portion in electrical contact with a first conductive pad 31a and a second portion in electrical contact with a second conductive pad 31b. The insulating layer 40 may have one or more holes 45 that have a shape substantially similar to a profile of the light emitter 50. The insulating layer 40 may have one or more holes 45 that have a shape substantially similar to the areas of intended electrical contact between the light emitter 50 and the conductive layer or the base 20 or both. For example, the insulating layer 40 may have one or more holes 45 that have a shape similar to that of an exposed anode of the light emitter 50, of an exposed cathode of the light emitter 50, of a ground of the light emitter 50, or any combination thereof.

The light emitter may comprise a light emitting surface 51 through which a substantial portion of the light generated by the light emitter is emitted.

Preferably, the light emitter 50 comprises a level-0 (L0) light emitting chip, though other compositions are also described herein. The light emitting chip may comprise a semiconductor (preferably a crystalline semiconductor, though non-crystalline variants are permissible), and may further comprise any combination of p-type and n-type semiconductors. The light emitting chip of any light emitter may be created using epitaxial growth and such growth may be upon a substrate that ultimately becomes part of a light emitting device 10 (for example, the light emitting chip may grow on the base 20 of a light emitting device 10) or the epitaxial growth of the light emitter may be on an intermediate substrate before being transferred to the final substrate (e.g., the base 20, the conductive layer 30, etc.) of the light emitting device 10. A few examples of possible L0 light emitting chips that may comprise the light emitter 50 of any embodiment include are those of Lumileds (e.g., the LUXEON FlipChip series of light emitting diodes), Samsung (e.g., LM101A, LM102A, LM131A, LH141A, etc.), and Seoul Semiconductor (e.g., WICOP series of light emitting diodes such as the Z8Y11, Z8Y15, Z8Y19, Z8Y22, etc.). The light emitter 50 may comprise one or more surface mount (SMT) light emitting diodes. In some embodiments the light emitting chip comprises a SMT light emitting diodes. The light emitter 50 may comprise one or more chip scale packages (CSPs) (e.g., an L0 CSP light emitting diode, an L1 CSP light emitting diode, etc.). In some embodiments, the light emitting chip comprises an L0 chip scale package (CSP). Those light emitting devices 10 comprising a light emitter 50 comprising an L0 light emitting chip may be referred to as L02 packages as they represent a hybrid of a level-0 chip with a level-2 (L2) cluster (one or more light emitting diode packages assembled on a substrate (e.g., a printed circuit board)), bypassing the intermediary level-1 light emitting diode package (a level-0 chip packaged with a combination of electrical connectors, mechanical connectors, physical protection, heat sinks, and/or optical components). In so doing the L02 packages described herein have an inherent advantage of being more compact and having a lower profile than a comparable L2 clusters.

Light of any color may be emitted by the light emitter 50 (such as red, orange, yellow, green, blue, purple, etc) of this or any embodiment. The light emitted by the light emitter 50 may comprise light of the visible light spectrum, the non-visible spectrum (e.g., infrared, ultraviolet, etc.), or any combination thereof, shown independently, sequentially, simultaneously, concurrently, or any combination thereof. Moreover, the color of the light emitted by the light emitter 50 may change over time such that at a first time a first color of light is emitted by the light emitter 50 and at a second time a second color of light is emitted by the light emitter 50. The light may be strobed, patterned, or focused, or any combination thereof. The light emitted by the light emitter 50 may have a color temperature from about 500 K to about 10,000 K. Some embodiments allow for the color temperature of the light emitted by the light emitter 50 to change over time or at the behest of a user such that at a first time the light emitted by the light emitter 50 has a first color temperature and light emitted by the light emitter 50 at a second time has a second color temperature. Light intensity, color, or color temperature of any light emitting device described herein may be changed during use (e.g., by altering the amount of current or potential received by the light emitter 50) or they may be they be changed in between use(s) (e.g., by switching out a first light emitter for a second light emitter).

The light emitter 50 of this or any embodiment may comprise a single LED die, a single LED, multiple LED dies, or multiple LEDs. The LED or multiple LEDs may provide white light, or any desired color. For example, the light emitter 50 may be of a type capable of covering any point along the International Commission on Illumination (CIE) 1931 color space and/or may be of a type capable of covering any point along the CIE 1976 color space (also known as the CIELUV color space). The light emitter 50 may be chosen for a particular embodiment to emit light of a single color or the light emitter 50 may emit light over a color gamut. One or more color gamuts may be covered by the light emitter 50 for those embodiments wherein two or more LED dies or two or more LED are used, such that the light emitter 50 may emit light selected from at least a first color gamut and emit light from at least a second color gamut. The first color gamut and the second color gamut may be the same. Preferably, the first color gamut and the second color gamut differ. The first and second color gamuts may be chosen for their respective effects; for instance, the first color gamut may comprise colors for clear illumination (such as a subset of colors corresponding to varying levels of white, blue, and yellow) and the second color gamut may comprise colors for treatment and/or healing (such as a subset of reddish colors). Light from the first and second color gamuts may be cast to a target region (e.g., a surgical site) simultaneously or sequentially. Light from the first and second color gamuts may be cast to the same target or they may be cast to a first and second target, respectively. The first and second target may overlap, but in this case, may not be equivalent. Furthermore, for those embodiments wherein the light emitter is comprised of multiple LED dies and/or multiple LEDs, the LEDs may provide different colors (such as red, green, or blue) and therefore the multiple LED dies and/or multiple LEDs may be adjusted to provide a desired color of light. The light emitter 50 may comprise an optical element (e.g., a lens, a lenslet) or may couple to an optical element (e.g., a lens, a waveguide) so as to mix the different colors of light for each of the individual LED dies or LEDs. What is desired in such cases is delivering a uniform light comprising the different colors of light to the target. Multiple colors may be used to provide varying shades of white colored light, or any other desired color which helps the surgeon or operator visualize and distinguish various objects such as tissue in the surgical field. Filters or coatings may be applied to any of the optical elements described herein (e.g., a lens, a lenslet, an optical waveguide, etc.) to filter specific frequencies of energy out.

The light emitter 50 of this or any embodiment may be selectively chosen to cover any point in CIE 1931 and/or any point in CIE 1976. The light emitter 50 may be monocolor or it may cover a color gamut. The light emitter 50 may be selectively chosen to emit any color or correlated color temperature (CCT) on the Planckian locus (also known as the black body locus) or the light emitter 50 may be selectively chosen to emit a single color or CCT on the Planckian locus. The light emitter 50 of this or any embodiment may have a color rendering index from about 50 to about 100, preferably from about 60 to about 100. In some embodiments the light emitter 50 may have a color rendering index from about 75 to 100.

Preferably, light emitted by the light emitter 50 is a bright, white light. To achieve this result, the light emitter 50 of this or any embodiment may comprise a die covered by a phosphor. For example, the light emitter 50 may comprise a blue die encased in a yellow phosphor (such as one made from cerium doped yttrium aluminum garnet (YAG:Ce) crystals) such that when the die emits blue light, a portion of that light is converted to yellow by the YAG:Ce. Combining the blue light of the die (which activates the blue receptors of human eyes) and the yellow light of the phosphor (which activates the red and green receptors of the eyes), may produce a light that appears white. Conversely, the light emitter 50 of this or any embodiment may comprise one or more light emitting chips that in combination produce a light that appears white. For example, three light emitting chips respectively emitting red, green, and blue may be used to produce light that appears white or two light emitting chips emitting blue light and yellow light may be used to produce light that appears white.

Dies or light emitting chips may be single color emitting dies such as blue light emitting diode (LED) dies, red light emitting diode dies, and/or green light emitting diode dies. Such single color emitting dies may or may not comprise, be coupled to, or lie adjacent of phosphor. L0 light emitting packages of this or any embodiment may comprise a single light emitting diode die, such as any of those described herein. L0 light emitting packages of this or any embodiment may comprise a multijunction light emitting diode (such as the Acrich series from Seoul Semiconductor) to emit one or more colors.

The light emitter 50 of this or any embodiment may comprise a light emitting diode (LED) (such as an XB-H LED from Cree), often referred to as a level-1 (L1) package.

The light emitter 50 of this or any embodiment may comprise a first portion of the light emitter 50 that is in contact with a first portion of the conductive layer 30 (e.g., the conductive pad 31*a*) and a second portion of the light emitter 50 that is in contact with a second portion of the conductive layer 30 (e.g., the conductive pad 31*b*). The first portion of the light emitter 50 in contact with the first portion of the conductive layer 30 and the second portion of the light emitter 50 in contact with the second portion of the conductive layer 30 may be electrically isolated from one another.

Figure 3A:
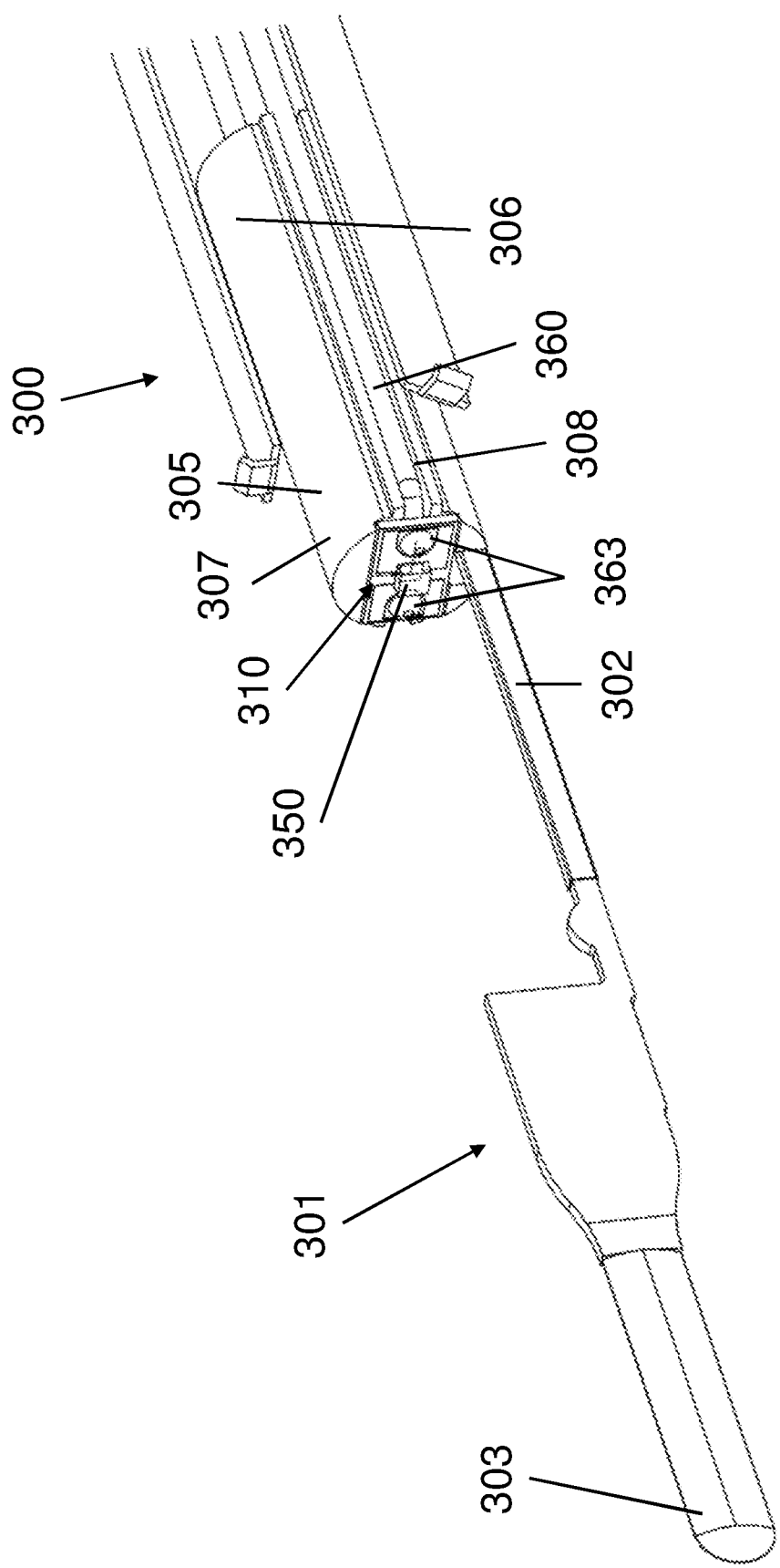
FIG. 3A shows bottom perspective view of an exemplary embodiment of an illuminated electrosurgical device comprising a light emitting package
Figure 3B:
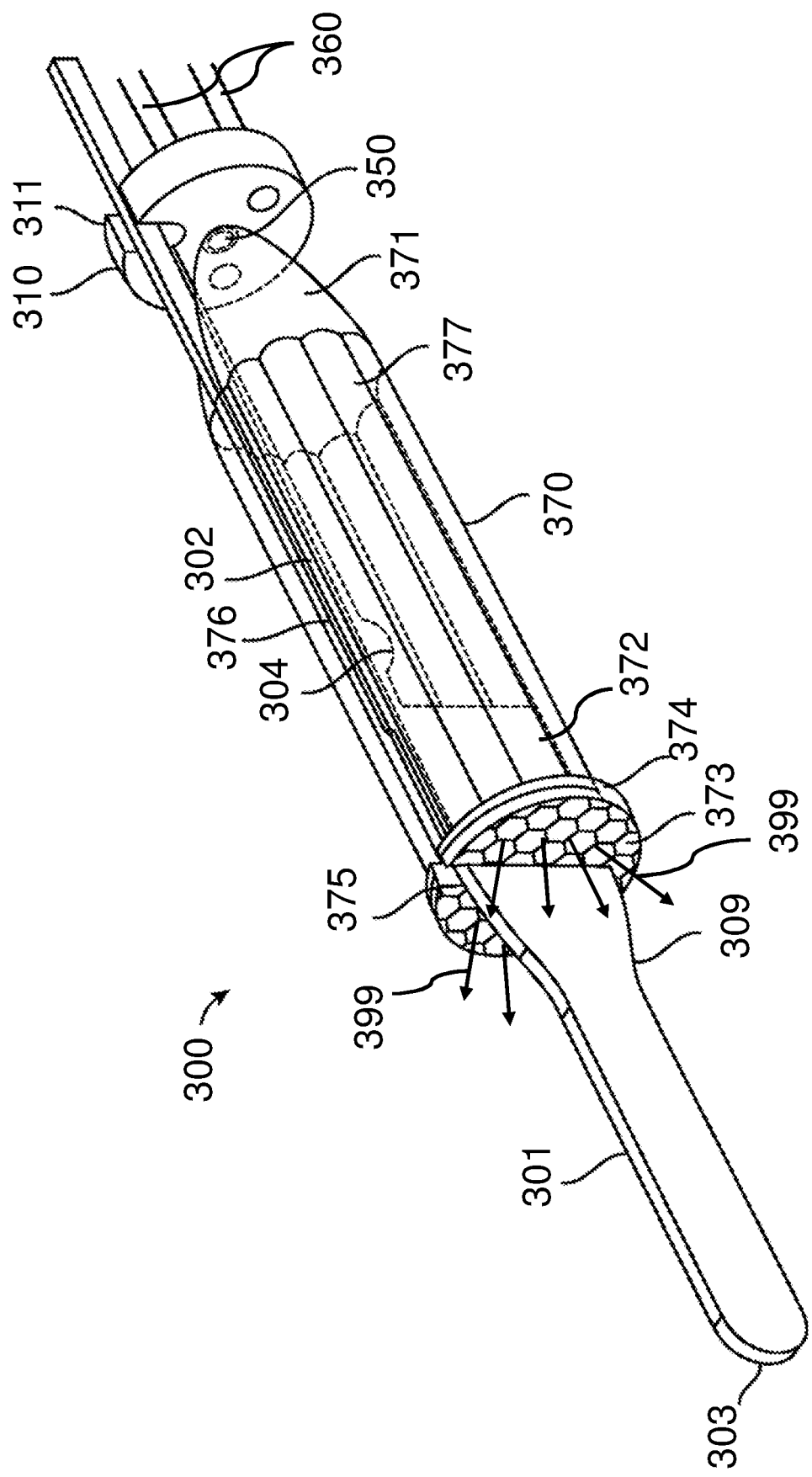
FIG. 3B shows top perspective view of the exemplary embodiment of an illuminated electrosurgical device comprising a light emitting package shown in FIG. 3A.

The light emitter 50 of this or any embodiment may optionally couple to a lens, a lenslet, an optical waveguide, or other any optical element that may guide or direct light from the light emitter 50 to a desired target location (e.g., onto a surgical field), as seen for example in FIG. 3B. The lens, one or more lenslets, optical waveguide, or any other optical element may be coupled to the light emitter 50 in any number of ways, including butt coupling to other coupling mechanisms, such as where the proximal end of q optical waveguide has a parabolic shape to capture q broad divergence of light emitted from the light emitter 50. Other means by which to couple the lens, one or more lenslets, optical waveguide, or any other optical element to the light emitter 50 include but are not limited to mechanical coupling (e.g., the optical element and the light emitter 50 have complimentary structures so that one fits or snaps into the other), interference fitting (e.g., the optical element may press into a portion of the light emitter 50 and be retained by the friction at the interface of the coupling), or adhesively bonded (e.g., a glue, an epoxy). Furthermore, the lens, one or more lenslets, optical waveguide, or any other optical element may be molded over the light emitter 50 (e.g., one or more individual dies of the light emitter 50 or the light emitter itself 50 may be dipped in a material that is preferably optically clear (e.g., a plastic, an epoxy, etc.) or held in a mold that is then injected with a material, wherein the material comprises lens, one or more lenslets, optical waveguide, or any other optical element.

Alternatively or in combination, the light emitter 50 of this or any embodiment may comprise a lens, a lenslet, an optical waveguide, or other any optical element that may guide or direct light from the light emitter 50 to a desired target location (e.g., onto a surgical field). For example, the lens, one or more lenslets, optical waveguide, or any other optical element may be molded with the light emitter 50 (e.g., one or more individual dies of the light emitter 50 or the light emitter itself 50 may be dipped in a material that is preferably optically clear (e.g., a plastic, an epoxy, etc.), held in a mold that is then injected with a material, or an amount of material may be added to the light emitter during manufacture, wherein the material comprises lens, one or more lenslets, optical waveguide, or any other optical element.

FIG. 1B shows the exemplary embodiment of the light emitting device 10 of FIG. 1A with a conductor element 60 extending through each of the one or more passageways defined by the combination of one or more holes 25 of the base 20 and one or more holes 35 of the conductive layer 30. The "wire" or "conductor element" herein may refer to any electrically conductive element, such as a wire, a pin, a filament, a fiber, a conductive track, a conductive pad, a conductive substrate, a foil, a laminate, and the like. In this illustrated example there are two passageways and each has a conductor element 60 disposed within them. Each of the conductor elements 60 has a proximal end 62 and a distal end (shown in FIG. 1C). The distal end may comprise a conductor element head 63. The conductor element head 63 may take on a number of shapes including but not limited to a flanged region wherein the flange of the conductor element head 63 extends beyond the nominal perimeter of the elongate portion of the conductor element 60, a sphere, a hemisphere, a cube, etc.

The conductor elements 60 may be in electrical contact with the conductive layer 30 (e.g., at the conductive pads 31a, 31b) at their distal end 61 or at the conductor element head 63, or both. Electrical contact between the conductor element 60 and the conductive layer 30 (such as through the conductive pads 31a, 31b) may be via a conductive edge (see the conductive edge 32 of FIG. 1A) or it may be via a conductive surface 33, or both. Electrical contact between the conductor elements 60 and the conductive layer 30 may be aided by a conductive intermediate medium such as solder, conductive epoxy, conductive paste, a conductive adhesive. Physical contact between the conductor elements 60 and light emitting device may include a loose fit, a tight fit, an interference fit, a press fit, or a fit wherein the shape of the conductor element 60 and the shape of its corresponding passageway may be similar, or any combination thereof.

The insulating layer 30 may or may not be in direct contact with the conductor element 60.

FIG. 1C shows an individual conductor element 60 similar to those shown in FIG. 1B. The conductor element 60 has a distal end 61 and proximal end 62. The distal end 61 may terminate in a conductor element head 63. The conductor element head 63 may comprise a flat lipped region that extends beyond the nominal perimeter of the conductor element 60. During manufacture (see FIG. 8) conductor element head 63 may have a first size and then be made to have a second, smaller, size (for instance, through grinding, milling, cutting, etc.).

Figure 2A:
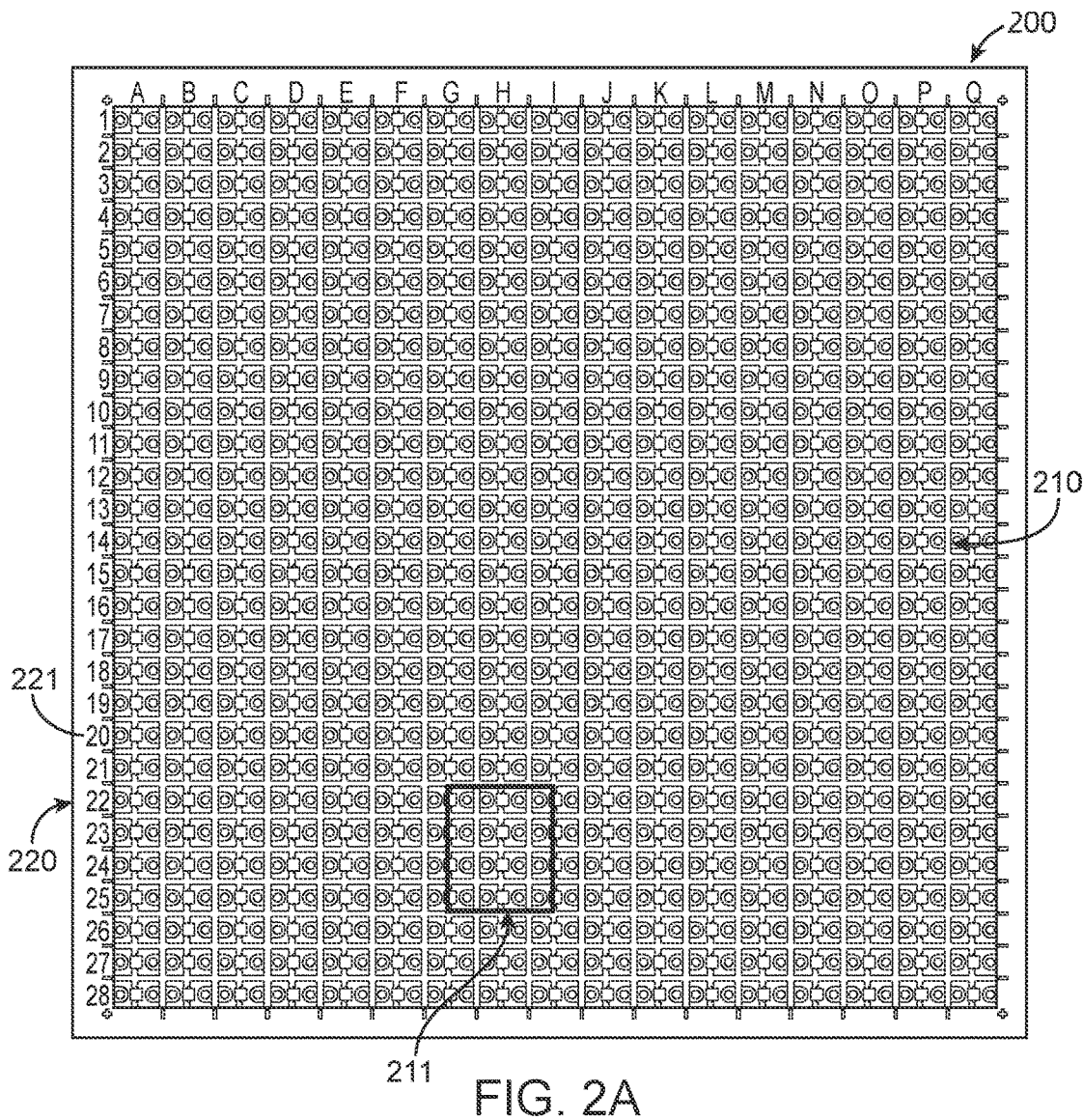
FIG. 2A shows an array of light emitting devices.
Figure 2B:
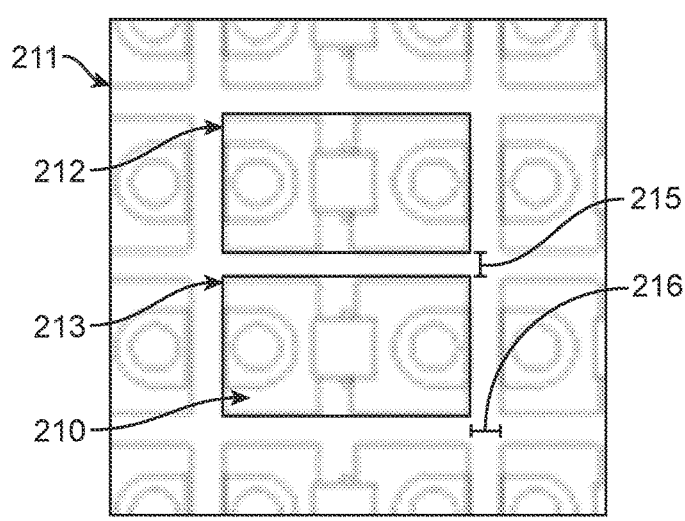
FIG. 2B shows a subset of light emitting devices from the array of light emitting devices shown in FIG. 2A.

FIG. 2A-2B show an array 200 of light emitting devices 210. Each of the light emitting devices 210 of this illustrated embodiment are of the type described in FIGS. 2A-2B, however, one of skill in the art will appreciate that the descriptions for FIGS. 2A-2B may apply any of the light emitting devices 210 described herein.

FIG. 2A shows the array 200 of light emitting devices 210 (e.g., those of the type describe in FIGS. 1A-1B). The array 200 of light emitting devices 210 may comprise a base 220, a conductive layer, an insulating layer, and one or more light emitters in accordance with the description herein. The base 220 may further comprise a base overhang 221. The overhang 221 may comprise a portion of the base without a conductive layer, without an insulating layer, or without a light emitter, or any combination thereof. Having a bare overhang 221 may allow for the array 200 of light emitting devices 210 to be coupled to another device for use (e.g., for illumination) or for further processing (e.g., separating one or more light emitting devices 210 from the array 200 of light emitting devices 210). For example, the overhang 221 may be clamped into a machine wherein the array 200 of light emitting devices 210 is cut with a saw blade or a laser to separate one or more light emitting devices 210 from the array 200 of light emitting devices 210.

FIG. 2B shows a subset 211 of the array 200 of light emitting devices 210 to better indicate the detail of the array 200 of light emitting devices 210 shown in FIG. 2A. Furthermore, two individual light emitting devices 212, 213 have each been marked with a box. The two individual light emitting devices 210 212, 213, each marked with a box, are of the type described in FIG. 1A-1B wherein the light emitting device 212, 213 comprises: a base; a conductive layer, wherein at least a portion of the conductive layer is coupled atop the base; an insulating layer wherein at least a first portion of the insulating layer is coupled atop the conductive layer and a second portion of the insulating layer is coupled atop the base; and a light emitter, wherein one or more holes, sized to receive a conductor element, extend through the base, the conductive layer, and the insulating layer). Between each individual light emitting device (e.g., light emitting device 212) and its nearest neighboring light emitting device (e.g., light emitting device 213) may be a first separation distance 215, also referred to herein as a first kerf distance. Between each individual light emitting device (e.g., light emitting device 212) and its nearest neighboring light emitting device (e.g., light emitting device 213) may be a second separation distance 216, also referred to herein as a second kerf distance. The first separation distance 215 and the second separation distance 216 may be approximately equal to a thickness of a saw blade used to separate one or more light emitting devices 210 from the array 200 of light emitting devices 210.

Though FIGS. 2A-2B show an array 200 of light emitting devices 210 in a rectilinear pattern, one should appreciate that any pattern of placement for the light emitting devices 210 among the array 200 of light emitting devices 210 may be used including, for example, a circular arrangement, a spiral, a cross-shape, an x-shape, a t-shape, etc.

FIG. 3A shows an electrosurgical system 300 with a light emitting device 310 disposed within. The electrosurgical system 300 may comprise a conductor element 301 (referred to here as an electrode or an electrosurgical tip) with a proximal portion 302 and a distal portion 303, a heat sink 305, a light emitting device 310 of any sort described herein (though this illustrated embodiment comprises one of the type shown in FIGS. 1A-1B and described in reference thereto), and conductor elements 360. Disposed between the light emitting device 310 and a portion of the electrode (e.g., the distal portion 303) may be an optical waveguide to direct light to a desired location in a surgical field (see, for example, FIG. 3B). Such a waveguide is preferably a non-fiber optic optical waveguide formed as a single integral piece (e.g., one that has been injection molded).

The electrosurgical system 300 may be of any type described in U.S. patent application Ser. No. 14/962,942 entitled "METHODS AND APPARATUS FOR ELECTROSURGICAL ILLUMINATION AND SENSING" or U.S. Provisional Patent Application No. 62/395,529 entitled "METHODS AND APPARATUS FOR ELECTROSURGICAL ILLUMINATION" the entire contents of which are incorporated herein by reference.

The electrode 301 may take on several form factors. For instance, the electrode 301 may be a thin flat blade (as illustrated), a cylindrical rod, a square rod, a wire, etc. The tip of the electrode 301 at the distal portion 303 thereof may be rounded, beveled, chisel-tipped, sharpened, etc. The electrode 301 may comprise a taper (best seen as the taper 309 of FIGS. 3B-3C) near its distal portion 303. Materials that may comprise the electrode 301 include individually or in combination but are not limited to aluminum, brass, bronze, carbon, carbon steel, copper, gold, iron, lead, lithium, mercury, molybdenum, nickel, palladium, platinum, silver, stainless steel, tin, titanium tungsten, or zinc. Preferably the electrode 301 would comprise a material resistant to material property changes in the face of current injection (such as, for instance, polarization capacitance). The electrode 301 may also comprise one or more materials to reduce reflection from light emitted by the light emitting device 310 or redirect light emitted from the light emitting device 310 to a target region.

The heat sink 305 of this or any embodiment may have the light emitting device 310 coupled at a distal portion 307 of the heat sink 305. Conductor elements 360 coupled to the light emitting device 310 may extend proximally through the heat sink 305. The heat sink 305 may comprise one or more channels 308 extending along the length of the heat sink 305, from about its distal portion 306 coupled to the light emitting device 310 to about its proximal portion 306. The one or more channels 308 of the heat sink 305 may be sized and shaped to conform to the conductor elements 360 such that the conductor elements 360 reside within the heat sink 305.

Alternatively or in combination, the heat sink 305 may comprise a heat sink to pull heat from the region away from the distal portion of the electrosurgical system 300 and/or to dissipate heat away from the region. Alternatively or in combination, the heat sink 305 may couple to a heat sink adapted to pull or dissipate heat from the region. The heat sink of any embodiment may comprise aluminum, copper, or their respective alloys. The heat sink of any embodiment may comprise one or more fins to aid in heat dissipation.

The conductor elements 360 may terminate at their distal portion in a conductor element head 363 in electrical contact with the light emitting device 310 as described herein. The conductor element head 363 may comprise an electrically conductive intermediate medium, such as solder. Examples of possible solder include but are not limited to $Sn_{50}Zn_{49}Cu_1$, $Sn_{95.5}Cu_4Ag_{0.5}$, $Sn_{90}Zn_7Cu_3$, $Pb_{90}Sn_{10}$, $Pb_{88}Sn_{12}$, $Pb_{85}Sn_{15}$, $Pb_{80}Sn_{20}$, $Pb_{75}Sn_{25}$, $Pb_{70}Sn_{30}$, $Pb_{68}Sn_{32}$, $Pb_{68}Sn_{30}Sb_2$, $Sn_{30}Pb_{50}Zn_{20}$, $Sn_{33}Pb_{40}Zn_{28}$, $Pb_{67}Sn_{33}$, $Pb_{65}Sn_{35}$, $Pb_{60}Sn_{40}$, $Pb_{55}Sn_{45}$, $Sn_{50}Pb_{50}$, $Sn_{50}Pb_{48.5}Cu_{1.5}$, $Sn_{60}Pb_{40}$, $Sn_{60}Pb_{38}Cu_2$, $Sn_{60}Pb_{39}Cu_1$, $Sn_{62}Pb_{38}$, $Sn_{63}Pb_{37}$, $Sn_{63}Pb_{37}P_{0.0015-0.04}$, $Sn_{62}Pb_{37}Cu_1$, $Sn_{70}Pb_{30}$, $Sn_{90}Pb_{10}$, $Sn_{95}Pb_5$, $Pb_{92}Sn_{50.5}Ag_{2.5}$, $Pb_{80}Sn_{12}Sb_8$, $Pb_{80}Sn_{18}Ag_2$, $Pb_{79}Sn_{20}Sb_1$, $Pb_{55}Sn_{43.5}Sb_{1.5}$, $Sn_{43}Pb_{43}Bi_{14}$, $Sn_{46}Pb_{46}Bi_8$, $Bi_{52}Pb_{32}Sn_6$, $Bi_{46}Sn_{34}Pb_{20}$, $Sn_{62}Pb_{36}Ag_2$, $Sn_{62.5}Pb_{36}Ag_{20.5}$, $Pb_{88}Sn_{10}Ag_2$, $Pb_{90}Sn_5Ag_5$, $Pb_{92.5}Sn_5Ag_{20.5}$, $Pb_{93.5}Sn_5Ag_{1.5}$, $Pb_{95.5}Sn_2Ag_{2.5}$, $In_{97}Ag_3$, $In_{90}Ag_{10}$, $In_{75}Pb_{25}$, $In_{70}Pb_{30}$, $In_{60}Pb_{40}$, $In_{50}Pb_{50}$, $In_{50}Sn_{50}$, $In_{70}Sn_{15}Pb_{9.6}Cd_{5.4}$, $Pb_{75}In_{25}$, $Sn_{70}Pb_{18}n_{12}$, $Sn_{37.5}Pb_{37.5}In_{25}$, $Pb_{90}In_5Ag_5$, $Pb_{92.5}In_5Ag_{2.5}$, $Pb_{92.5}In_5Au_{2.5}$, $Pb_{94.5}Ag_{5.5}$, $Pb_{95}Ag_5$, $Pb_{97.5}Ag_{2.5}$, $Sn_{97.5}Pb_1Ag_{1.5}$, $Pb_{97.5}Ag_{1.5}Sn_1$, $Pb_{54}Sn_{45}Ag_1$, $Pb_{96}Ag_4$, $Pb_{96}Sn_2Ag_2$, $Sn_{61}Pb_{36}Ag_3$, $Sn_{56}Pb_{39}Ag_5$, $Sn_{98}Ag_2$, $Sn_{65}Ag_{25}Sb_{10}$, $Sn_{96.5}Ag_{3.0}Cu_{0.5}$, $Sn_{95.8}Ag_{3.5}Cu_{0.7}$, $Sn_{95.6}Ag_{3.5}Cu_{0.9}$, $Sn_{95.5}Ag_{3.8}Cu_{0.7}$, $Sn_{95.25}Ag_{3.8}Cu_{0.7}Sb_{0.25}$, $Sn_{95.5}Ag_{3.9}Cu_{0.6}$, $Sn_{95.5}Ag_4Cu_{0.5}$, $Sn_{96.5}Ag_{3.5}$, $Sn_{96}Ag_4$, $Sn_{95}Ag_5$, $Sn_{94}Ag_6$, $Sn_{93}Ag_7$, $Sn_{95}Ag_4Cu_1$, $Sn$, $Sn_{99.3}Cu_{0.7}$, $Sn_{99}Cu_{0.7}Ag_{0.3}$, $Sn_{97}Cu_3$, $Sn_{97}Cu_{2.75}Ag_{0.25}$, $Zn_{100}$, $Bi_{100}$, $Sn_{91}Zn_9$, $Sn_{85}Zn_{15}$, $Zn_{95}A_{15}$, $Sn_{91.8}Bi_{4.8}Ag_{3.4}$, $Sn_{70}Zn_{30}$, $SnsoZn_{20}$, $Sn_{60}Zn_{40}$, $Pb_{63}Sn_{35}Sb_2$, $Pb_{63}Sn_{34}Zn_3$, $Pb_{92}Cd_8$, $Sn_{48}Bi_{32}Pb_{20}$, $Sn_{89}ZnsBi_3$, $Sn_{83.6}Zn_{7.6}In_{8.8}$, $Sn_{86.5}Zn_{5.5}In_{4.5}Bi_{3.5}$, $Sn_{86.9}In_{10}Ag_{3.1}$, $Sn_{95}Ag_{3.5}Zn_1Cu_{0.5}$, $Sn_{95}Sb_5$, $Sn_{97}Sb_3$, $Sn_{99}Sb_1$, $Sn_{99}Ag_{0.3}Cu_{0.7}$, $Sn_{96.2}Ag_{2.5}Cu_{0.8}Sb_{0.5}$, $Sn_{88}In_{8.0}Ag_{3.5}Bi_{0.5}$, $Bi_{57}Sn_{42}Ag_1$, $Bi_{58}Sn_{42}$, $Bi_{58}Pb_{42}$, $In_{80}Pb_{15}Ag_5$, $Pb_{60}In_{40}$, $Pb_{70}In_{30}$, $Sn_{37.5}Pb_{37.5}In_{26}$, $Sn_{54}Pb_{26}In_{20}$, $Pb_{81}In_{19}$, $In_{52}Sn_{48}$, $Sn_{52}In_{48}$, $Sn_{58}In_{42}$, $Sn_{51.2}Pb_{3.6}Cd_{18.2}$, $Sn_{77.2}In_{20}Ag_{2.8}$, $In_{74}Cd_{26}$, $In_{61.7}Bi_{3.8}Cd_{7.5}$, $Bi_{47.5}Pb_{25.4}Sn_{12.6}Cd_{9.5}In_5$, $Bi_{48}Pb_{25.4}Sn_{12.8}Cd_{9.6}In_4$, $Bi_{49}Pb_{18}Sn_{15}In_{18}$, $Bi_{49}Pb_{18}Sn_{12}In_{21}$, $Bi_{50.5}Pb_{27.8}Sn_{12.4}Cd_{9.3}$, $Bi_{50}Pb_{26.7}Sn_{13.3}Cd_{10}$, $Bi_{44.7}Pb_{22.6}In_{19.1}Cd_{5.3}Sn_{8.3}$, $In_{60}Sn_{40}$, $In_{51.0}Bi_{32.5}Sn_{16.5}$, $Bi_{49.5}Pb_{27.3}Sn_{13.1}Cd_{10.1}$, $Bi_{50.0}Pb_{25.0}Sn_{12.5}Cd_{12.5}$, $Bi_{50.0}Pb_{31.2}Sn_{18.8}$, $Bi_{50}Pb_{38}Sn_{22}$, $Bi_{56}Sn_{30}In_{14}$, $Cd_{95}Ag_5$, $Cd_{82.5}Zn_{17.5}$, $Cd_{70}Zn_{30}$, $Cd_{60}Zn_{40}$, $Cd_{78}Zn_{17}Ag_5$, $Sn_{40}Zn_{27}Cd_{33}$, $Zn_{90}Cd_{10}$, $Zn_{60}Cd_{40}$, $Cd_{70}Sn_{30}$, $Sn_{50}Pb_{32}Cd_{18}$, $Sn_{40}Pb_{42}Cd_{18}$, $Zn_{70}Sn_{30}$, $Zn_{60}Sn_{40}$, $Zn_{95}Sn_5$, $Sn_{90}Au_{10}$, $Au_{80}Sn_{20}$, $Au_9Si_2$, $Au_{96.8}Si_{3.2}$, $Au_{87.5}Ge_{12.5}$, $Au_{82}In_{18}$, and $In_{100}$.

FIG. 3B (and its subsequent exploded view seen FIG. 3C) shows the electrosurgical system 300 of FIG. 3A with a waveguide 370 (e.g., an optical waveguide) disposed between the light emitting device 310 and the distal portion 303 of the electrode 301.

The waveguide 370 has a proximal portion 371 and a distal portion 372. The proximal portion 371 may be shaped to capture the divergence of light emitted from the light emitter 350. For example, the proximal portion 371 may be parabolic in shape. Furthermore, the ratio of diameter of the waveguide 370 and the diameter of the light input region of the waveguide 370 may lie anywhere within the range from about 100:1 to about 1:1, preferably from about 30:1 to about 2:1, and more preferably about 5:1. The distal portion 372 comprises a light emitting surface made of light extracting features 373 so that light 399 may be extracted from the waveguide 370 and cast onto a target region (e.g., a surgical site). The distal portion 372 may optionally further comprise a rim 374 which may serve as a surface against which the inner surface of a covering (not illustrated) may abut. Said covering may comprise a metal tube that may further act as a heat sink or means by which to transfer thermal energy away from the inner body of the electrosurgical system 300. Cladding 377 may extend along the length of the waveguide 370 to aid in the light transmitting efficiency (by, for example, increasing internal reflectance) of the waveguide 370.

The waveguide 370 may comprise a channel 376 sized to receive the elongate proximal portion 302 of the electrode 301. Moreover, the waveguide 370 may comprise a recessed region (best seen in FIG. 3C) that matches a protrusion 304 of the electrode 301 so that the electrode 301 is constrained and held in place. The channel 376 may extend distally along the length of the waveguide 370, creating a slit 375 in the distal portion 372 of the waveguide 370. The slit 375 may be sized to receive the electrode 301.

The waveguide 370 of this or any embodiment may comprise one or more of acrylic, polycarbonate, cyclo-olefin polymer, cylco-olefin copolymer, or malleable silicones. In any embodiment of a waveguide, the waveguide may be a solid or hollow cylindrical shape, as well as other shapes. The waveguide may also have a constant cross-section, or the waveguide may be tapered or flared.

The light emitting device 310 may be of any sort described herein. Alternatively or in combination, the light emitting device 310 may comprise a slot 311 sized to receive a portion of an electrode 301 and/or one or more conductors 360.

Figure 4A:
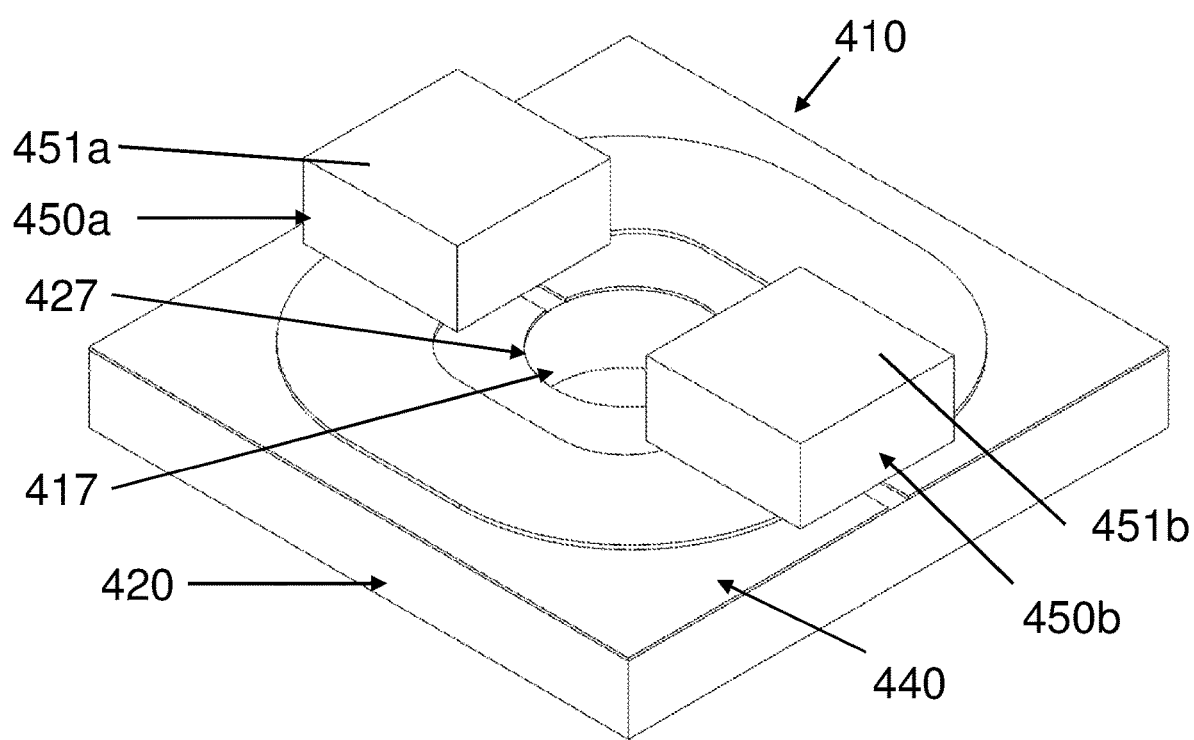
FIG. 4A shows an exemplary embodiment of a light emitting device with two light emitters.
Figure 4B:
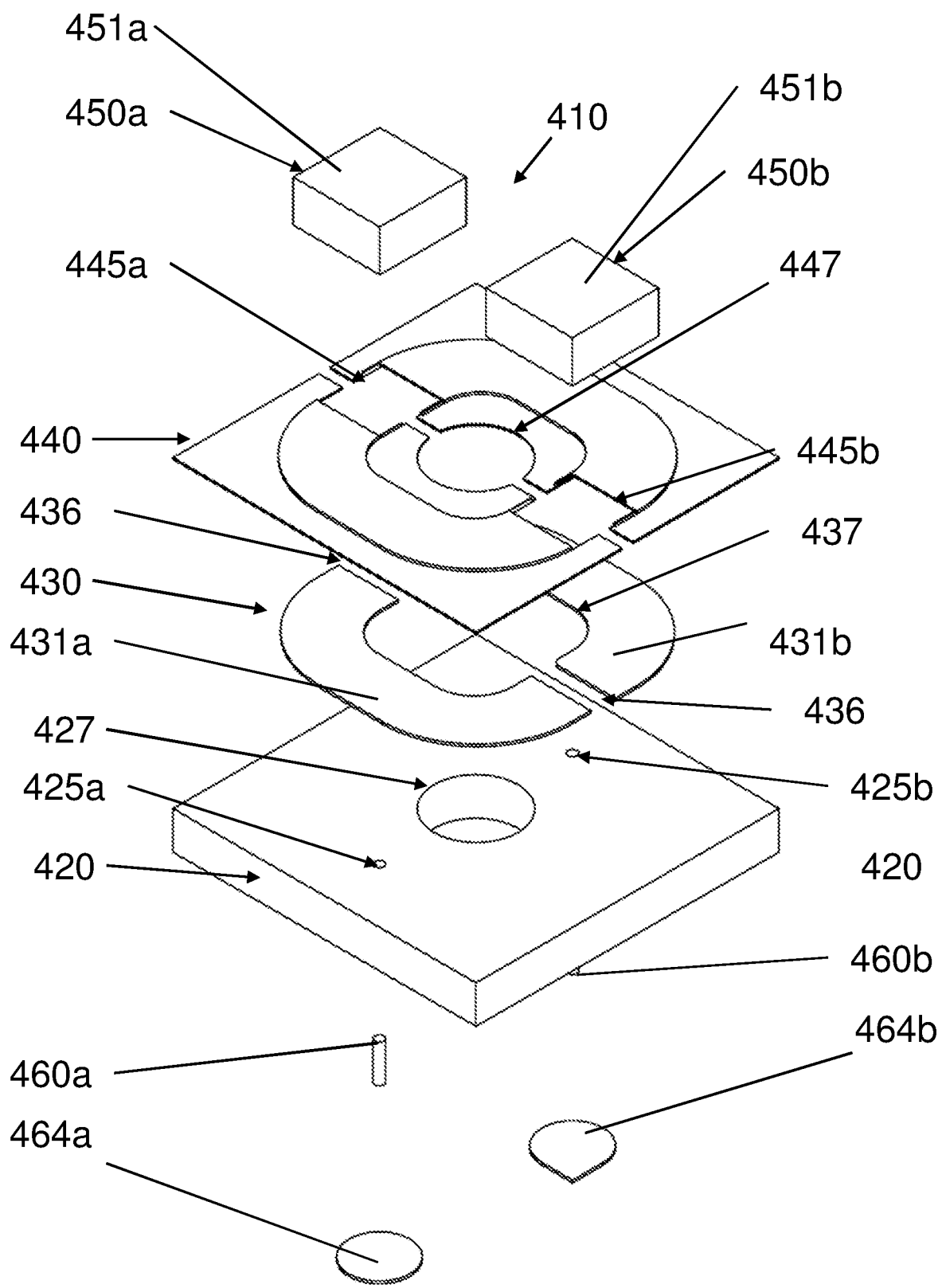
FIG. 4B shows an exploded view of FIG. 4A.

FIG. 4A-4B show an exemplary embodiment of a light emitting device 410 with two light emitters 450a, 450b.

FIG. 4A shows a perspective view of a light emitting device 410 comprising a base 420 with a through-hole 427, a conductive layer (best seen in FIG. 4B), an insulating layer 440, two or more light emitters 450a, 450a (each comprising a light emitting surface 451a, 451b) and a passageway 417 for a surgical device (such as an electrode for electrosurgery) to pass through. The passageway 417 may substantially conform to the perimeter of the surgical device. Though the light emitting device 410 is shown with a substantially square perimeter, the light emitting device 410 may have a perimeter of any shape, such as a circle, an oval, an ellipse, a triangle, etc.

FIG. 4B shows an exploded view of the light emitting device 410. The light emitting device 410 may comprise a base 420, a conductive layer 430, an insulating layer 440, and two or more light emitters 450a, 450b.

The base 420 may comprise any material described herein including but not limited to one or more thermally conductive and electrically non-conductive materials (e.g., in composite form, as an alloy, etc.) such as alumina (e.g., $Al_2O_3$), aluminum nitride, aluminum oxide, aluminum oxide ceramic substrate, boron nitride, boron nitride powder, ceramic, corundum cubic boron nitride (such as Borazon®), gas pressure sintered silicon nitride, high strength substrate alumina, hot-pressed aluminum nitride, hot-pressed boron nitride, hot-pressed silicon nitride, microplasmic anodizing ceramic coatings (e.g., for aluminum, magnesium, titanium, zirconium, etc.), pyrolytic boron nitride, silicon nitride (e.g., $Si_3N_4$, $Si_3N_4$—$Y_2O_3$, etc.), sintered alumina, sintered reaction bonded silicon nitride, zirconia, zirconia toughened alumina. Other possible materials that may be used as an alternative to or in combination with any of the aforementioned materials include aluminum, gold, silver, cobalt, chromium, copper, iron, magnesium, nickel, lead, platinum, steel, titanium, tin, silicon, tungsten, zinc. Preferably the base 20 is comprised of at least one material with a thermal conductivity greater than about 20 W/m-K. Preferably the base 20 is comprised of at least one material with an electrical resistivity greater than about $10^{10}$ ohm-cm. Even more preferably the base 20 is comprised of at least one material with a thermal conductivity greater than about 20 W/m-K and an electrical resistivity greater than about $10^{10}$ ohm-cm.

The base 420 may comprise a through-hole 427. The through-hole 427 of the base 420 may correspond in size and shape as the hole 447 in the insulation layer 440. The through-hole 427 of the base 420 may allow one or more surgical devices to be passed through or held in place, such as a scalpel or an electrode for electrosurgery. Alternatively or in combination, two or more holes 425a, 425b may be disposed on the base 420 to allow two or more conductor elements 460a, 460b to pass therethrough.

The conductive layer 430 of this or any embodiment may comprise two or more conductive pads 431a, 431b. The conductive pads 431a, 431b may be separated by a gap 436 to keep the conductive pads 431a, 431b from electrically contacting each other. The conductive layer 430 may have a hole 437 sized to allow the passage of one or more medical devices (such as an electrode for electrosurgery). The size and/or shape of the hole 437 may conform to the size and/or shape of the through-hole 427 of the base 420 or the size and/or shape of the hole 437 may conform to the size and/or shape of the hole 447 of the insulating layer 440, or both, or neither. The perimeter of the hole 437 may be less than, about equal to, or greater than the perimeter of the through-hole 427 of the base 420 or the perimeter of the hole 437 may be less than, about equal to, or greater than the perimeter of the hole 447 of the insulating layer 440. Though illustrated as two approximately U-shaped halves, the conductive pads 431a, 431b of the conductive layer 430 may take on any shape including a square-like U-shaped half, Y-shaped, linear, curved, circular, etc. One of the two or more conductive pads (e.g., the conductive pad 431a) may correspond to an anode while another of the two or more conductive pads (e.g., the conductive pad 431b) may correspond to a cathode. Similarly, one of the two or more conductive pads (e.g., the conductive pad 431a) may correspond to an anode while another of the two or more conductive pads (e.g., the conductive pad 431b) may correspond to a ground. Furthermore, one of the two or more conductive pads (e.g., the conductive pad 431a) may correspond to a cathode while another of the two or more conductive pads (e.g., the conductive pad 431b) may correspond to a ground.

The insulating layer 440 may be of any type described herein. In the illustrated example, the insulating layer 440 comprises a pair of holes 445a, 445b each corresponding to an individual light emitter (450a and 450b, respectively). The shape and size of the holes 445a, 455b may substantially correspond to the shape and size of the light emitter 450a, 450b. Alternatively, the perimeter of the holes 445a, 445b may be less than, about equal to, or greater than the perimeter of the light emitter 450a, 450b. The holes 445a, 445b must permit each of the light emitters 451a, 451b to be in electrical contact with the conductive layer 430, preferably through contact with the conductive pads 431a, 431b.

The light emitters 450a, 450b may be of any type described herein. For example, the two or more light emitters 450a, 450b may comprise a light emitting diode (LED) (such as an XB-H LED from Cree). Each light emitter 450a, 450b may comprise a light emitting surface 451a, 451b through which a substantial portion of the light generated by the light emitter is emitted.

Conductor elements 460a, 460b (such as wires, pins, etc.) may through the base 420 to bring the conductive layer 430 (for instance, the conductive pads 431a, 431b of the conductive layer 430) into electrical contact with proximal conductive pads 464a, 464b. The proximal conductive pads 464a, 464b of this or any embodiment may comprise one or more electrically conductive materials (e.g., in composite form, as an alloy, etc.), such as aluminum, brass, bronze, carbon, carbon steel, copper, gold, iron, lead, lithium, mercury, molybdenum, nickel, palladium, platinum, silver, stainless steel, tin, titanium tungsten, or zinc. One of the two or more proximal conductive pads 464a, 464b may be of a different shape than that of the other two or more proximal conductive pads 464a, 464b. For example, in FIG. 4B the proximal conductive pad 464a is a circle whereas the proximal conductive pad 464b is tear drop shaped (or approximately three-quarters of a circle and one quarter of a square). Differentiation among the proximal conductive pads 464a, 464b may allow a user or a machine to know what sort of electrical energy to apply to each of the proximal conductive pads 464a, 464b. In some embodiments, the shape of the proximal conductive pads 464a, 464b uniquely identifies what sort of electrical energy (e.g., positive or negative potentials) is to be applied to each of the proximal conductive pads 44a, 464b.

Figure 5A:
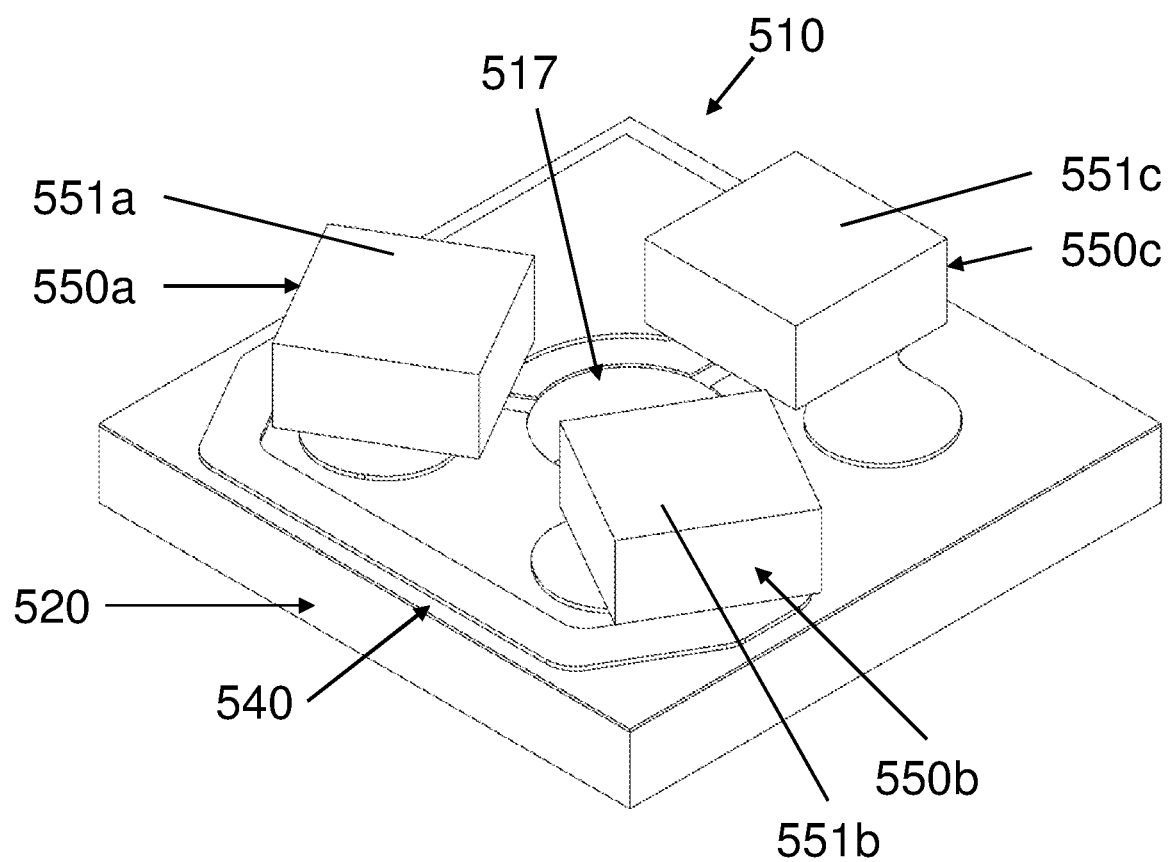
FIG. 5A shows an exemplary embodiment of a light emitting device with three light emitters.
Figure 5B:
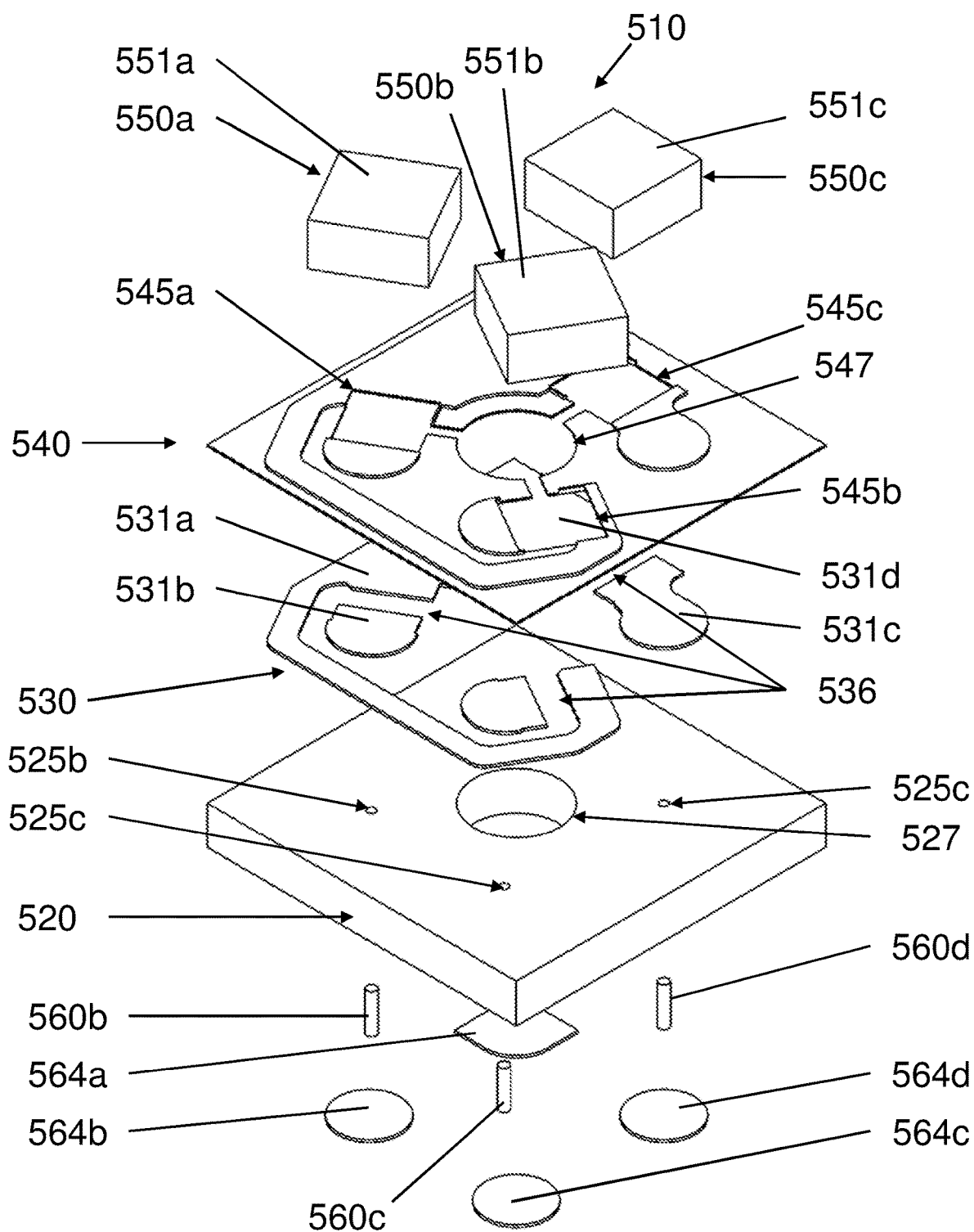
FIG. 5B shows an exploded view of FIG. 5A.

FIG. 5A-5B shows an exemplary embodiment of a light emitting device 510 with three light emitters 550a, 550b, 550c. The illustrated light emitting device 510 comprises a base 520 with holes for electrical connectivity (holes 525a, 525b, 525c, 525d) and a through-hole 527 to allow for the passage or placement of a surgical device (such as an electrode for an electrosurgical device), a conductive layer 530 comprising four distinct conductive pads (a conductive pad 531a shared in common amongst the light emitters 550a, 550b, 550c and three light emitter specific conductive pads 531b, 531c, 531d), an insulating layer 540 comprising holes 545a, 545b, 545c corresponding to each of the light emitters 550a, 550b, 550c and a hole 547 through which a surgical device may pass, and three light emitter 550a, 550b, 550c. Proximal to the posterior surface of the base 520 reside four proximal conductive pads 564a, 564b, 564c, 564d that may be in electrical contact with the conductive layer 530 (e.g., via the conductive pads 531a, 531b, 531c, 531d) through conductor elements 560a, 560b, 560c, 560d passed through the holes 525a, 525b, 525c, 525d of the base 520.

The conductive layer 520 may comprise one conductive pad 531a in electrical contact with each of the three or more light emitters 551a, 551b, 551c and corresponding conductive pads 531b, 531c, 531d that are in electrical contact with only one of the three or more light emitters 551a, 551b, 551c. The one conductive pad 531a in electrical contact with each of the three or more light emitters 551a, 551b, 551c may be offset by a gap 536 from the other conductive pads 531b, 531c, 531d. The gap 536 may be constant between each conductive pad 531a, 531b, 531c, 531d, or it may vary for each or along the length of each.

Figure 6:
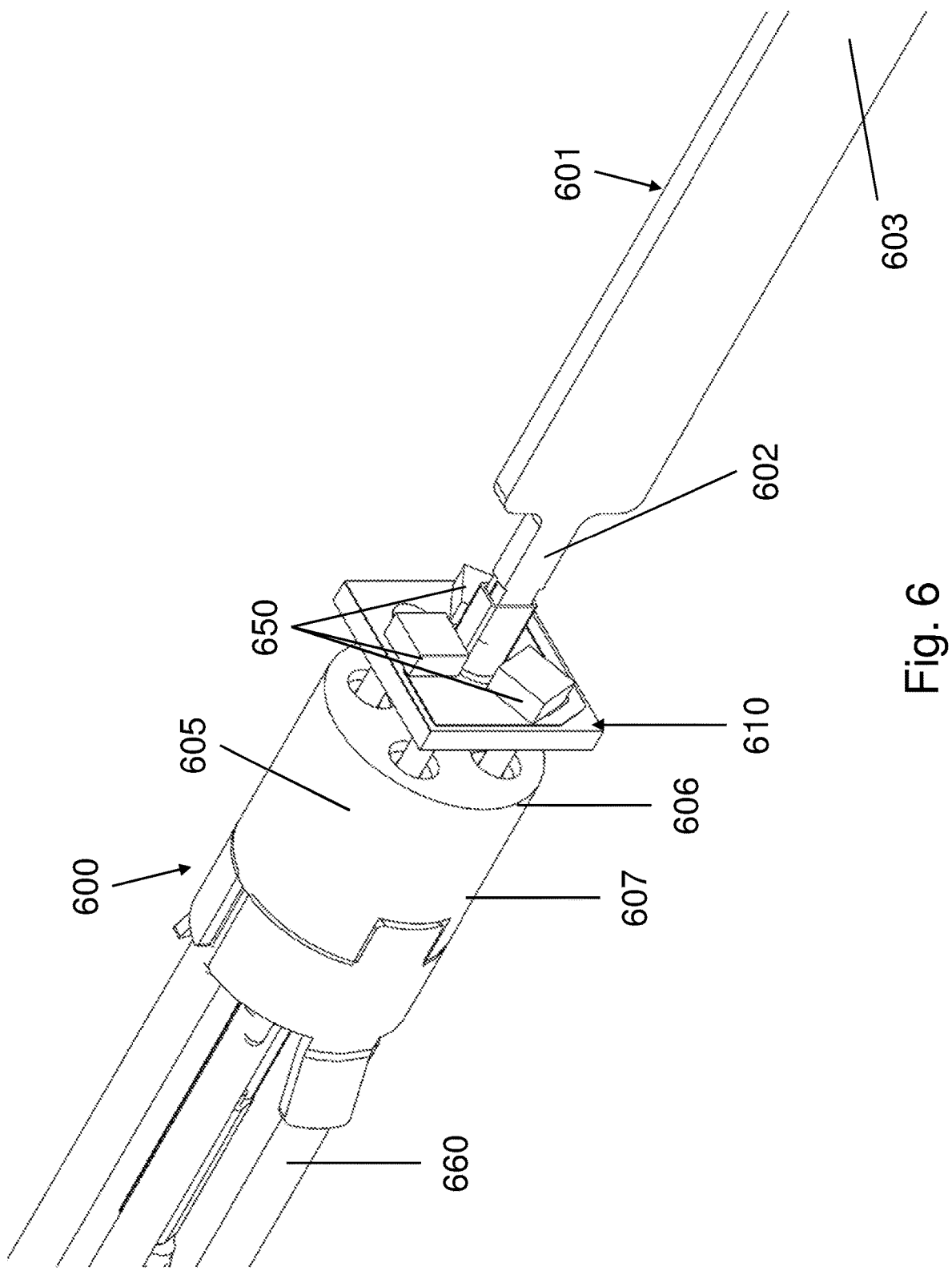
FIG. 6 shows an electrosurgical system comprised of a light emitting device with three light emitters.

FIG. 6 shows an electrosurgical system 600 comprising a light emitting device 610 with three light emitters 650, similar to that shown in FIGS. 5A-5B and described. The electrosurgical system 600 may comprise a conductor element 601 (such as an electrode, electrosurgical tip, etc.) with a proximal portion 602 and a distal portion 603, a heat sink 605 with a proximal portion 607 and a distal portion 606, a light emitting device 610 with three light emitters 650, and conductor elements 660 extending proximally down the length of the electrosurgical system 600. Though the light emitting device 650 shown may resemble that shown and described in FIGS. 5A-5B, it should be appreciated that any light emitting device described herein may be used.

The conductor element 601 of the illustrated electrosurgical system has a proximal portion 602 of a conductor element 601 disposed within a passageway of the light emitting device 650; the proximal portion 602 extending proximally through the light emitting device such that at least a portion of the proximal portion 602 resides proximally of the light emitting device 650 and/or at least a portion of the conductor element 601 extends distally beyond the light emitting device 650. The conductor element 601 may have at least a portion of the proximal portion 602 that is sized and/or shaped to be disposed within the passageway of the light emitting device 650.

The heat sink 605 may be of any type described herein. The heat sink 605 may comprise a proximal portion 607 and a distal portion 606. At the distal portion 606 may be coupled the light emitting device 650. Coupling of the light emitting device to the distal portion 606 of the heat sink 605 may be via press fitting, interference fitting, mechanical bonding, chemical bonding, an adhesive, an epoxy, held by wires (e.g., the conductor elements 660), or soldered, or any combination thereof. The heat sink 605 may comprise grooves or channels (not illustrated) that allow one or more conductor elements 660 to pass through the proximal portion 607 of the heat sink 605 to the distal portion 606. The conductor elements 660 extending through the grooves or channels may extend beyond the distal portion 606 of the heat sink 605. Conductor elements 660 extending beyond the distal portion 606 of the heat sink 605 may comprise ends that terminate in male type pins or female type pin receivers to aid in establishing electrical contact with one or more proximal conductive pads (not shown) of the light emitting device 650. The conductor elements 660 extending through the grooves or channels may extend beyond the proximal portion 607 of the heat sink 605. Those conductor elements 660 that extend beyond the proximal portion 606 of the heat sink 605 may comprise an insulating layer such that no two conductor elements 660 come to be in direct electrical contact.

Figure 7A:
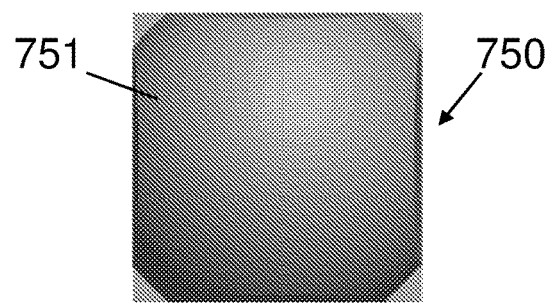
FIG. 7A shows a top view of an exemplary embodiment of a light emitter.
Figure 7B:
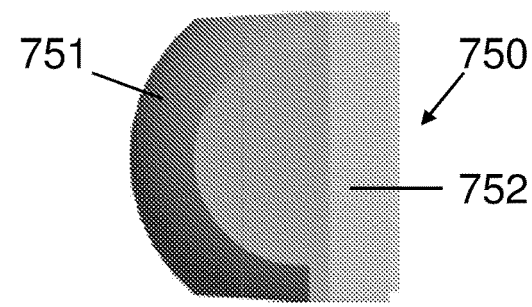
FIG. 7B shows a side view of the exemplary embodiment of the light emitter of FIG. 7A.
Figure 7C:
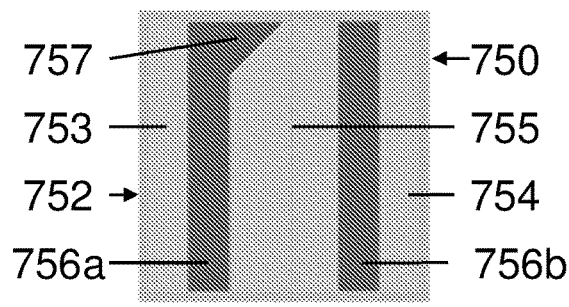
FIG. 7C shows a bottom view of the exemplary embodiment of the light emitter of FIGS. 7A-7B.

FIG. 7A-7C show top, side, and bottom views of an exemplary embodiment of a light emitter 750. The light emitter 750 may be of any type described herein. For example, the illustrated embodiment of FIGS. 7A-7C represents a light emitter 750 comprising a light emitting diode (LED), such as an XB-H LED from Cree. The light emitter 750 may comprise a light emitting surface 751 (as seen best in FIGS. 7A-7B), a base 752 (best seen in FIGS. 7B-7D), two or more conductive pads 753, 754 (best seen in FIGS. 7C-7D), and one or more non-conductive regions 756a, 756b (best seen in FIGS. 7C-7D).

FIG. 7A shows a top view of the light emitter 750 comprising a light emitting surface 751 on the anterior portion of the light emitter 750. As illustrated, the light emitter 750 may have a square profile when viewed from the top. The light emitter 750 may have either as an alternative to or in combination with a square profile, a circular profile, an oval profile, an ellipse-like profile, a polygonal profile, or a rectangular profile when viewed from the top.

FIG. 7B shows a side view of the light emitter 750 comprising a light emitting surface 751 coupled to an anterior surface of the base 752. The light emitting surface 751 may be curved, as shown in the illustrated embodiment, or, alternatively or in combination, the light emitting surface 751 may be square-like, hemispherical, polygonal, or be comprised for stepped light extracting features.

FIG. 7C shows a bottom view of the light emitter 750 comprising the base 752 with two or more conductive pads 753,754 and one or more non-conductive regions 756a, 756b. One of the two or more conductive pads 753, 754 (e.g., conductive pad 753) may receive one type of electrical energy (for example, a negative voltage) while another of the two or more conducive pads 753, 754 (e.g., conductive pad 754) may receive another type of electrical energy (for example, a positive voltage). One of the two or more conductive 753, 754 may be ground while another of the two or more conductive pads receives a first type of electrical energy (for example, positive voltage or negative voltage).

One or more of the one or more non-conductive regions (in this case, non-conductive region 756a) may comprise a flag 757 for identifying its nearest conductive pad (in this case conductive pad 753) as one which is to receive a first type of electrical energy. In this exemplary embodiment the flag 757 resides near an outer edge of the non-conductive region 756a.

Figure 7D:
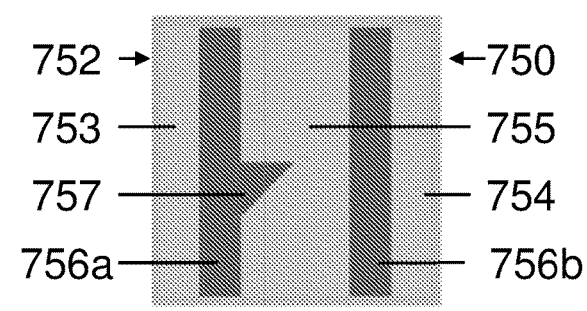
FIG. 7D shows a bottom view of the exemplary embodiment of the light emitter of FIGS. 7A-7C with an alternative bottom.

FIG. 7D shows a bottom view of a light emitter 750 with an alternative arrangement on its bottom surface, namely, the flag 757 identifying its nearest conductive pad as one which is to receive a first type of electrical energy now resides towards the middle of the non-conductive region 756a. The identifying flag 757 of any embodiment may any shape or form within the one or more non-conductive regions 756a, 756b.

In some embodiments (as illustrated in FIGS. 7C-7D), the light emitter 750 may comprise a support region 755.

The light emitter 750 may be of any sort described herein. Furthermore, the light emitter 750 may have a color temperature from about 500 K to about 10,000 K. The light emitter 750 of this or any embodiment may have a luminous flux (at about 700 mA) greater than at least about 150 lm.

Figure 8:
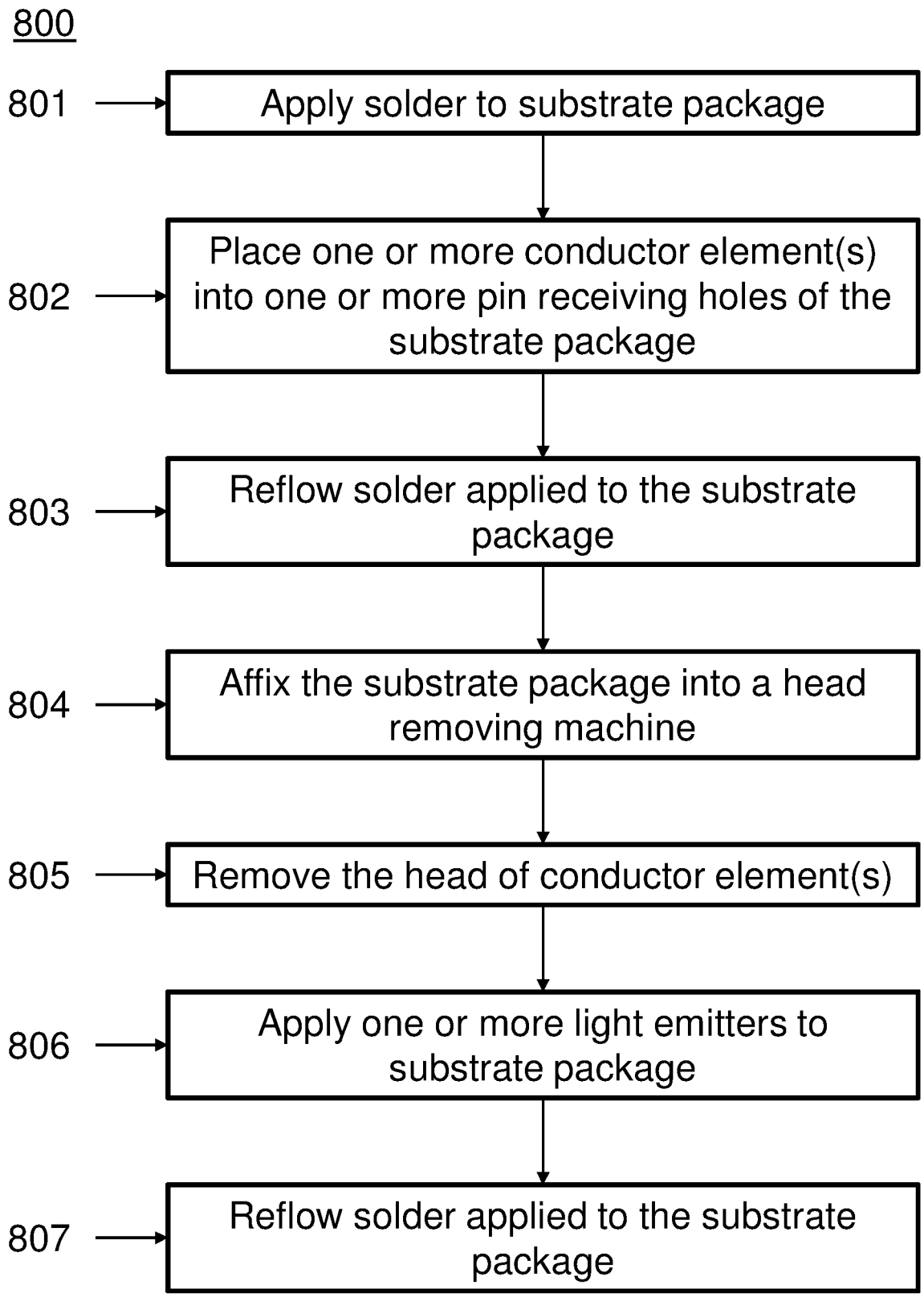
FIG. 8 shows a method of manufacture for light emitting devices.

FIG. 8 shows a method 800 of manufacturing light emitting devices as described herein. All steps listed in FIG. 8 for method 800 are optional and may be combined in any order. The method 800 may be preceded by or include an operation for selecting one or more conductor elements (of any sort described herein, such as a pin or wire) to be used, such as a 4068 Mill-Max pin. The method 800 may comprise one or more of the following steps in any combination: an operation 801 comprising applying solder (e.g., as a paste) to a substrate package (wherein the substrate package may comprise a combination of a base, a conductive layer, and an insulating layer); an operation 802 comprising placing one or more conductor elements (e.g., a pin, a wire, etc.) into one or more conductor element receiving holes of the substrate package (wherein the conductor element receiving holes are those matched holes of the base, conductive layer, and insulating layer sized and shaped to receive a conductor element (e.g., pin, wire, etc.) also referred to as a "passageway," "channel," and "corridor" throughout); an operation 803 comprising reflowing solder applied to the substrate package (for example, by placing the substrate into a reflow oven); operation 804 comprising affixing the substrate package into a machine to remove excess material (referred to in the figure as a "head") from the conductor element (such as by clamping the substrate package along an overlapping portion of the base into a grinding machine); operation 805 comprising removing the heads (also referred to throughout as conductor element heads, wire heads, pin heads, etc.) of the conductor elements, for example via grinding, milling, laser machining, etc., such that the top of the conductor element(s) may be about level with the insulating layer and/or solder mask (approximately 25 micrometers or less); operation 806 comprising applying one or more light emitters to the substrate package; and operation 807 comprising reflowing solder applied to the substrate package to fix the light emitters in place and establish electrical contact between the light emitters and the conductive elements (such as the conductive layer, conductive pads, conductor elements, pins, wires, etc.).

The one or more conductor elements may be chosen to have a minimal head profile so that light output from the light emitting device created via method 800 may be maximized without the need to remove the conductor element head, thereby through a method 800 comprising operations 801, 802, 803, 806, and 807 (without optional steps operations 804 and 805). The conductor element used in any embodiment of the method 800 described herein may comprise a conductor element head with an initial thickness from about 25 microns to about 500 micrometers, preferably from about 100 micrometers to about 500 micrometers, or even more preferably from about 150 micrometers to about 500 micrometers. For those embodiments of method 800 wherein the one of more conductor elements requires removing excess conductor element material, preferably the conductor element head may have a final thickness of less than 100 micrometers and even more preferably less than 25 micrometers.

FIGS. 9A-9H show top views of exemplary embodiments of a light emitting device 910 comprising a first layer 930 and a second layer 940 atop a base 920. The first layer 930 and second layer 940 of the illustrated embodiments may each individually or collectively be of any type of layer described herein (e.g., a conductive layer, an insulating layer, etc.). For the sake of clarity and simplicity (but in no way suggesting this is the only possible arrangement), the first layer 930 is generally discussed with regards to FIGS. 9A-9H as a conductive layer and the second layer 940 is generally discussed with regards to FIGS. 9A-9H as an insulating layer. It should be appreciated that the converse is true as is the case where both the first layer 930 and the second layer 940 are conductive layers or both the first layer 930 and the second layer 940 are an insulating layer.

Figure 9A:
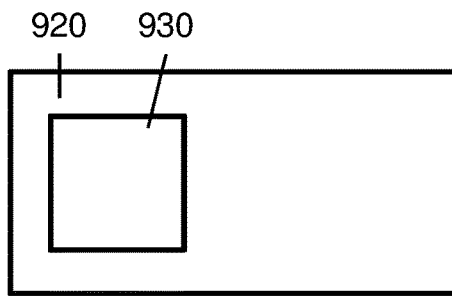
FIGS. 9A-9H show top views of exemplary embodiments of a light emitting device comprising a first layer and a second layer.

FIG. 9A shows an exemplary embodiment of a light emitting device 910 comprising a base 920 of any sort described herein and a first layer 930 (e.g., a conductive layer) coupled to the top surface of the base 920. The conductive layer 930 may be disposed over at least a portion of the base 920. In some embodiments the conductive layer 930 may be disposed over an entire surface (such as the top surface or the bottom surface) of the base 920. Though illustrated as rectangular, the base 920 and the conductive layer 930 may be of any shape, such as a circle, an ellipse, a strip, etc.

Figure 9B:
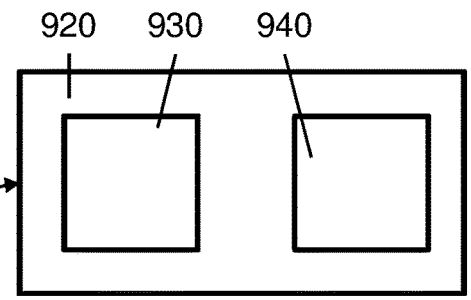

FIG. 9B shows an exemplary embodiment of a light emitting device 910 comprising a base 920 of any sort described herein, a first layer 930, and a second layer 940. In the illustrated example, the first layer 930 (e.g., a conductive layer) and the second layer 940 (e.g., an insulating layer) are each on top of the base 920 such that no portion of the base 920 is covered by both a conductive layer 930 and an insulating layer 940. Moreover, in the illustrated embodiment, there is no overlap of the conductive layer 930 and the insulating layer 940. For such embodiments one of the layers (e.g., the second layer 940) may surround one of the other layers (e.g., the first layer 930). The first layer 930 and the second layer 940 may abut each other.

Figure 9C:
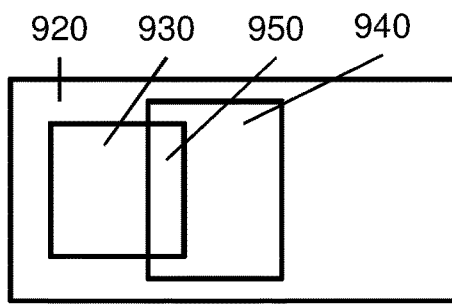

FIG. 9C shows an exemplary embodiment of a light emitting device 910 comprising a base 920 of any sort described herein, a first layer 930, a second layer 940, and a region of overlap 950. The overlap 950 may comprise at least a portion of the first layer 930 and at least a portion of the second layer 940 in physical contact. The overlap 950 may comprise either the first layer 930 overlapping the second layer 940 (such that the second layer 940 of the region of overlap 950 is in physical contact with the base 920 while the first layer 930 of the region of overlap 950 is in physical contact with the second layer 940) or the second layer 940 overlapping the first layer 930 (such that the first layer 930 of the region of overlap 950 is in physical contact with the base 920 while the second layer 940 of the region of overlap 950 is in physical contact with the first layer 930) or any combination thereof. For those embodiments wherein the first layer 930 is a conductive layer and the second layer 940 is an insulating layer and wherein the second layer 940 overlaps the first layer 930 in a region of overlap 950, the region of overlap 950 represents an area where the otherwise exposed conductive layer is insulated such that little to no current passes directly through the top surface of the region of overlap 950.

In the illustrated embodiment of FIG. 9C the first layer 930 comprises a first portion in contact with the base 920 and otherwise exposed and a second portion constituting the overlap 950 and the second layer 940 comprises a first portion in contact with the base 920 and otherwise exposed and a second portion constituting the overlap 950.

Figure 9D:
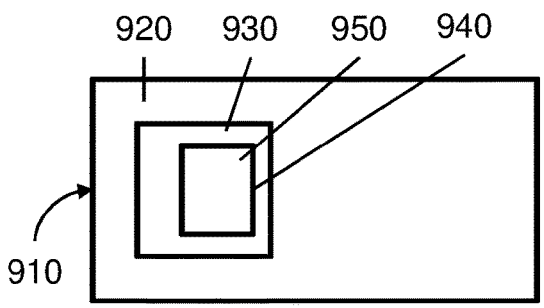

FIG. 9D shows an exemplary embodiment of a light emitting device 910 comprising a base 920 of any sort described herein, a first layer 930, and a second layer 940 that comprises a region of overlap 950. In this case, the entirety of the second layer 940 may overlap the first layer 930 such that the first layer 930 is in contact with the base and the second layer 940 while the second layer 950 physically contacts the top of the first layer 940 or the second layer 940 may be coupled to the surface of the base 920 and the first layer 930 may completely overlap the second layer 940 and contact the surface of the base 920. For example, the first layer 930 may comprise a conductive layer and the second layer 940 disposed on top of the first layer 930 may comprise a solder mask so that the overlap 950 represents a region of the conductive layer that is insulated.

Figure 9E:
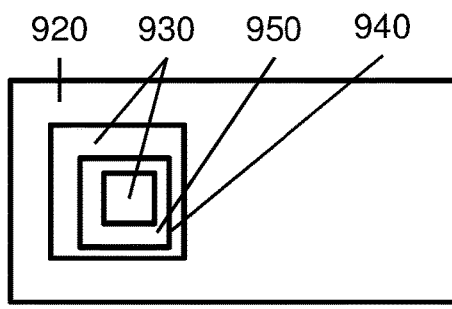

FIG. 9E shows an exemplary embodiment of a light emitting device 910 similar to that shown in FIG. 9D with the notable difference being that the region of overlap 950 is donut-shaped, thereby creating a perimeter of overlap encircling and being encircled by regions of the first layer 930 that are exposed.

Figure 9F:
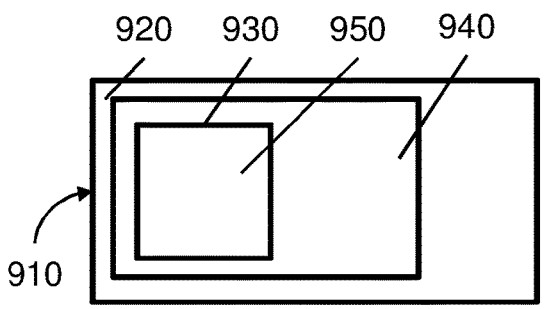

FIG. 9F shows an exemplary embodiment of a light emitting device 910 comprising a base 920 of any sort described herein, a first layer 930 that comprises a region of overlap, and a second layer 940. In this case, the entirety of the first layer 930 may overlap or be overlapped by the second layer 940. The first layer 930 may be sandwiched between the base 920 and the second layer 940, permitting the second layer 940 to lay top both the base 920 and the first layer 930. The first layer 930 may lay atop the second layer 940 to create the region of overlap 950, though it should be appreciated that this is similar to that described with regard to FIG. 9D.

In the illustrated example of FIG. 9F, the first layer 930 may comprise a conductive layer and the second layer 940 disposed on top of the first layer 930 may comprise a solder mask so that the overlap 950 represents a region of the conductive layer that is insulated.

Figure 9G:
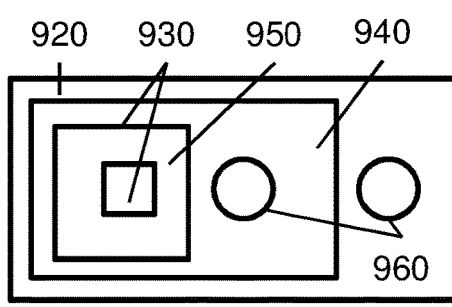

FIG. 9G shows an exemplary embodiment of a light emitting device 910 comprising a base 920, a first layer 930, a second layer 940, a region of overlap 950 wherein the first layer 930 and the second layer 940 lay atop one another (e.g., the first layer 930 on top of the second layer 940 or the second layer on top of the first layer), and one or more holes 960. The holes 960 of this or any embodiment may pass through the base 920, the first layer 930, the second layer 940, the region of overlap 950, or any combination thereof. For example, the illustrated embodiment demonstrates a hole 960 passing through both the base 920 and through the combination of the base 920 and the second layer 940.

Figure 9H:
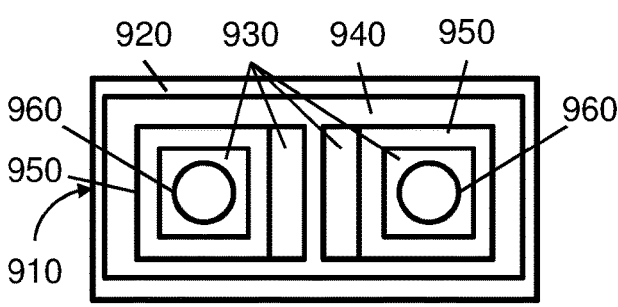

FIG. 9H shows an exemplary embodiment of a light emitting device 910 comprising a base 920, a first layer 930, a second layer 940, one or more regions of overlap 950, and one or more holes 960. Given the complexity that may arise from all possible permutations of the disclosure as represented by the preceding figures (FIGS. 9A-9G), it should be appreciated that though a description will be given for the illustrated example (FIG. 9H), other exemplary embodiments suggested by the disclosure are possible and intended.

The light emitting device 910 of FIG. 9H shows a first layer 930 overlapped by a second layer 940 in two regions of overlap (950). The first layer 930 further comprises at least two distinct regions: a first region wherein the first layer 940 is atop the base 920 and is otherwise not contacted by the second layer 940 and a second region wherein the first layer 930 and the second layer 940 comprise a region of overlap 950 (the region of overlap being of any sort described herein, such as the first layer 930 on top of the second layer 940, the second layer 940 on top of the first layer 930, or any combination thereof). The first layer 930 may further comprise exposed regions wherein the bottom surface of first layer 930 layer contacts the top surface of the base 920 and the top surface of the first layer 940 is otherwise exposed (e.g., not contacted by the second layer 940 or the base 920). One or more exposed regions of the first layer 930 may be sized and/or shaped to receive one or more conductive pads of a light emitter (such as those shown and described in FIGS. 7C-7D), one or more support regions of a light emitter (such as those shown and described in FIGS. 7C-7D), one or more conductor elements (such as those shown and described in FIGS. 1A-1C, FIGS. 3A-3C, and FIG. 6), one or more conductor element heads (such as those shown and described in FIGS. 1A-1C and FIG. 3A), or one or more electrodes (such as those shown and described in FIGS. 3A-3C, FIG. 6, and FIG. 11A-11C), or any combination thereof. Furthermore, the holes 960 may similarly be size and/or shaped to receive to receive one or more conductive pads of a light emitter (such as those shown and described in FIGS. 7C-7D), one or more support regions of a light emitter (such as those shown and described in FIGS. 7C-7D), one or more conductor elements (such as those shown and described in FIGS. 1A-1C, FIGS. 3A-3C, and FIG. 6), one or more conductor element heads (such as those shown and described in FIGS. 1A-1C and FIG. 3A), or one or more electrodes (such as those shown and described in FIGS. 3A-3C, FIG. 6, and FIG. 11A-11C), or any combination thereof, or the holes 960 may be of any type described herein.

The second layer 940 further comprises at least two distinct regions: a first region wherein the second layer 940 is atop the base 920 and is otherwise not contacted by the first layer 930 and a second region wherein the second layer 940 and the first layer 930 comprise a region of overlap 950 (the region of overlap being of any sort described herein, such as the first layer 930 on top of the second layer 940, the second layer 940 on top of the first layer 930, or any combination thereof).

Figure 10A:
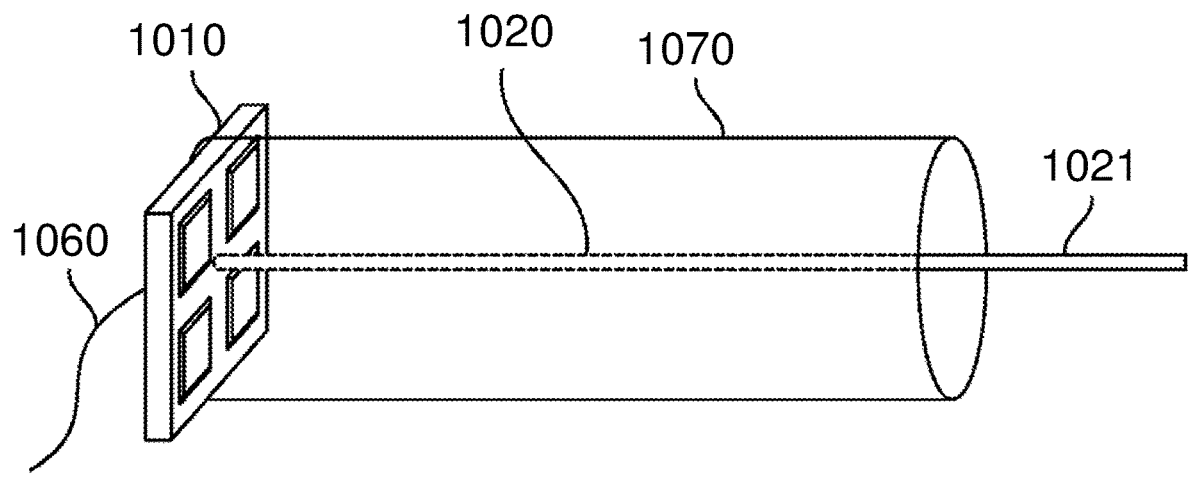
FIGS. 10A-10B show exemplary embodiments of a light emitting device coupled with an optical element.
Figure 10B:
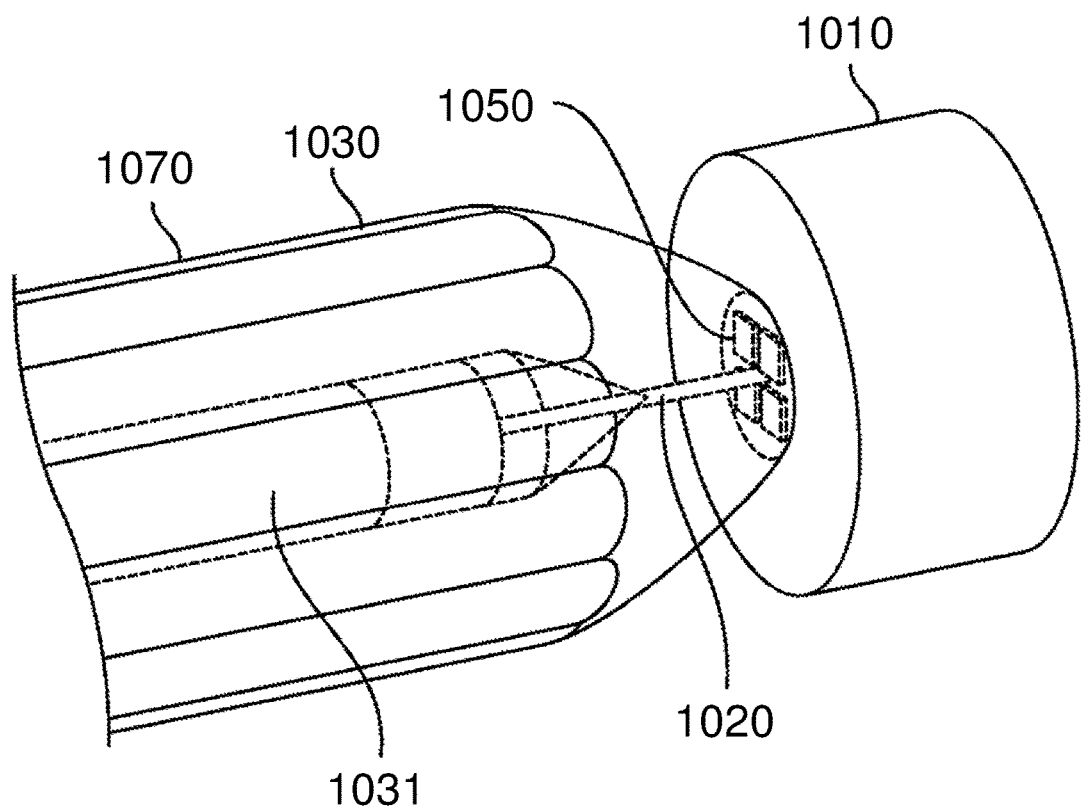

FIGS. 10A-10B show an exemplary illumination device comprising a light emitting device 1010, a conductor element 1020 (that shall be referred to for the descriptions of FIGS. 10A-10B as an "electrode") coupled to the light emitting device 1010 (as described herein), a conductor element 1060 (that shall be referred to for the descriptions of FIGS. 10A-10B as a "wire"), and an optical element 1070 coupled to the light emitting device 1010. The electrode 1020 may comprise a distal portion 1021 that is not surrounded by the optical element 1070. The optical element 1070 is intended to either extract light from the light emitting device 1010 (typically via a coupling with one or more light emitters 1050), receive light from the light emitting device 1010, transmit light from the light emitting device 1010, or direct light from the light emitting device 1010 onto a target region (e.g., a surgical field), or any combination thereof. To aid in the optical transmission aspects of the illumination device, a cladding 1030 may be disposed on a surface of the optical element 1070, a cladding 1031 may be disposed on a surface of the electrode 1020, or both. The optical element 1070 of this or any embodiment may be of any type described herein including the lens, one or more lenslets, or an optical waveguide.

Figure 11A:
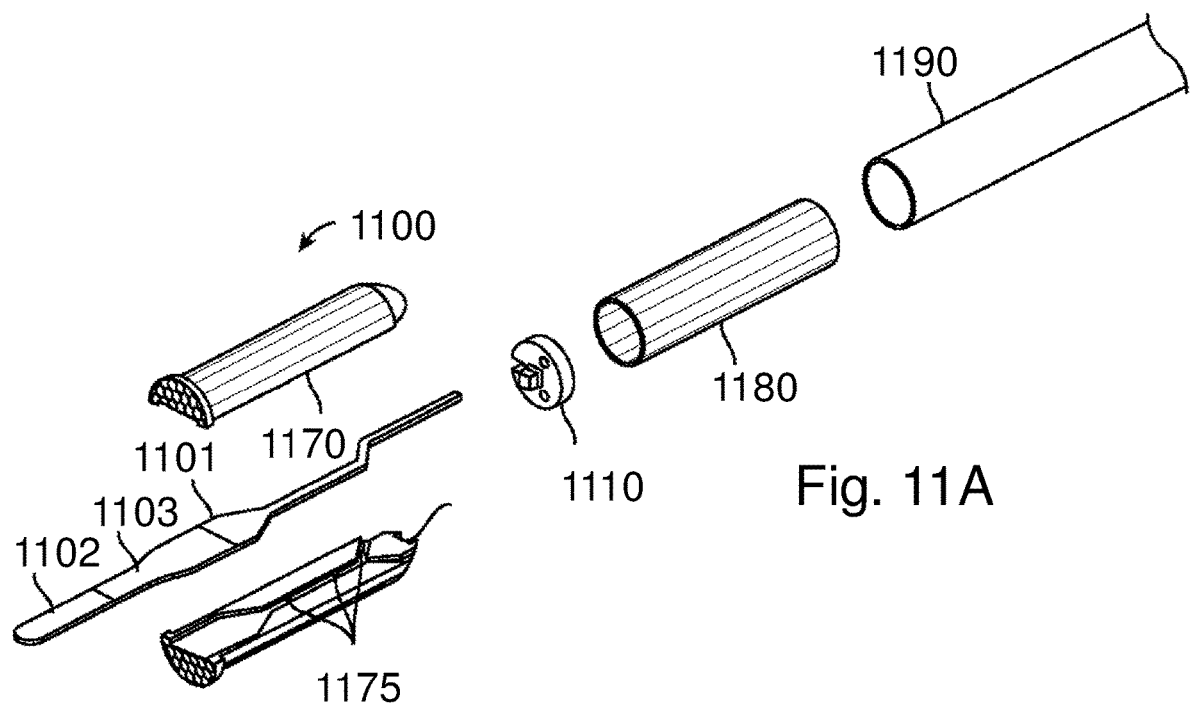
FIGS. 11A-11C show an exemplary embodiment of an illuminated electrosurgical device comprising a light emitting package.
Figure 11B:
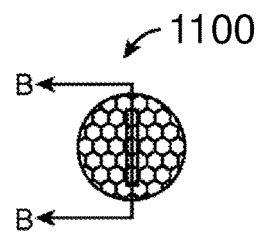
Figure 11C:
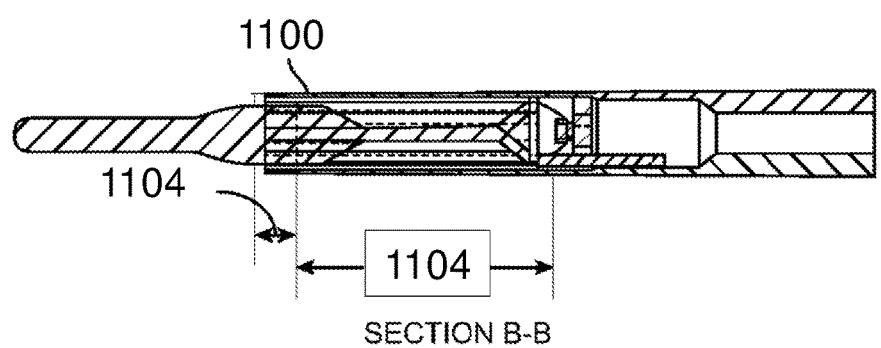

FIGS. 11A-11C show an exemplary embodiment of an illuminated electrosurgical device comprising a light emitting package.

FIG. 11A shows an exploded view of another exemplary embodiment of an illuminated electrosurgical device 1100 which may be coupled to a handpiece such as an electrosurgical pencil (not illustrated). One advantage of this embodiment is that the light and the electrode may be rotated together, thereby ensuring uniform lighting of the target tissue. The illuminated electrosurgical device 1100 includes an anodized aluminum shaft 1190, FEP cladding 1180, a light emitting device 1110, waveguide halves 1170, and an electrode blade 1101. The waveguide may be molded as a single unit as described elsewhere in this specification, and therefore does not necessarily have two halves coupled together.

The electrode blade 1101 preferably includes a distal portion which is used to deliver energy (preferably RF energy) to tissue in order to cut or coagulate the tissue. This distal section 1102 is preferably insulated with a layer of material, here preferably a glass coating. The glass coating is advantageous since it has desirable optical properties and is distal to the waveguide 1170 and therefore helps to ensure that light emitted therefrom is properly reflected from the waveguide toward the surgical target area and minimizes glare back toward the surgeon or other operator. The tip is preferably insulated by a Teflon (polytetrafluorinated ethylene, PTFE) coating. This coating will scatter and absorb light. Having a reflective surface on the tip will aid the efficiency of the device by reflecting the light from the waveguide off the surface of the tip towards the target and therefore reduce unnecessary scatting. The tip can also have various shapes to aid in dispersion of light. The tip may have a curvature or taper. For example, FIG. 19BA illustrates a top view of an electrode 1902. FIG. 19B shows a cross-section of the electrode 1902 taken along the line B-B and shows upper and lower flat planar surfaces while FIGS. 19C and 19D show optional convex upper and lower surfaces. The distal portion may be thin enough to allow an operator to bend the tip in order to conform to the anatomy being treated. A middle section 1103 of the electrode blade 1101 is preferably also insulated, here preferably with FEP (fluorinated ethylene propylene) in order to prevent energy from leaking out of the electrode along the middle section, and also the FEP provides an index of refraction lower than the index of refraction of the waveguide 1170 thereby helping to prevent or minimize light leakage from the waveguide due to contact between the waveguide and electrode blade. A low index of refraction coating or air gaps may also be used in conjunction with or instead of FEP to provide similar results. A proximal portion of the electrode includes a thin elongate section which serves as a conductor element and allows the electrode to be coupled to wires in the handle (not shown) which are operably connected to the power supply, preferably an RF generator. The proximal portion of the electrode may be straight and linear, or it may have an angled section so that a proximal portion of the thin elongate section is off-center, allowing it to pass through the Light emitting device 1110 off center. Optionally, the proximal portion of the electrode may also be straight and pass through the center of the Light emitting device.

Waveguide halves 1170 may be snap fit, adhesively bonded, ultrasonically welded together or otherwise joined together, sandwiching the electrode in between the two waveguide halves. The waveguide halves form a cylindrical shape around the electrode, thereby illuminating around the electrode. The distal portion of the waveguide may include a lens, a plurality of lenslets or other optical features which help shape the light emitted therefrom. In this embodiment, the optical waveguide has an outer surface that is multi-faceted forming a polygon which approximates a cylinder. This extraction surface of the waveguide may be flat or curved or even angled or tapered to provide better light directionality, for example with respect to divergence of the light. Having a plurality of facets allows better mixing of light as it passes through the waveguide. Standoffs 1175 in a channel in each half of waveguide prevent direct contact between the waveguide and the electrode, thereby minimizing contact and subsequent light loss. The channel in each half of the waveguide preferably matches the shape of the electrode which lies therein.

Light emitting device 1110 includes one or more light emitters as described herein for providing light which passes through the waveguide. The light emitting device 1110 may be any of the LED or any other light sources described in this specification. The light emitter may also be parabolically shaped to help focus and deliver the light to the waveguide. In some embodiments, the conductor portion of the electrode may pass through the center of the Light emitting device, or the conductor may pass off center through the Light emitting device.

A layer of FEP cladding is disposed over the waveguide and may be heat shrunk down on the two halves, thereby securing the two together. Optionally in conjunction with the FEP cladding or as an alternative to the FEP cladding, other optical coatings may be used in this or any of the embodiments disclosed herein in order to provide a low index of refraction material adjacent the waveguide to prevent or minimize light loss. Also, an air gap may be disposed against the waveguide to help minimize or prevent light loss since the air gap would provide a lower index of refraction adjacent the waveguide. An outer-most aluminum tube 1190 or other heat conductive material, is then disposed over the FEP cladding and helps keep the components together and also serves as a heat sink to remove heat buildup. This tube is coupled to the LED core to dissipate the heat. The entire assembly may then be coupled to a handpiece and it may telescope in or out of the handpiece. A locking mechanism (not shown) such as a collet or quarter turn lock may be used to lock the electrode in position once it has been telescoped into a desired position.

FIG. 11B is an end view of the illuminated electrosurgical device 1100, and FIG. 11C is a cross-section taken along the line B-B in FIG. 11B. FIG. 11C highlights the FEP coated section 1120, as well as the section of electrode 1122 coupled with standoffs 1175 to minimize direct contact between the electrode and the waveguide.

In any of the embodiments described herein, the waveguide may also be a lens or have a lens portion for controlling light delivered from the waveguide. Therefore, the waveguide with or without a lens, or a separate lens may be mounted on or otherwise coupled to the light emitting device or illumination element being used. Optionally, and embodiment may therefore include an optical element such as a lens mounted in front of the illumination element such as any light emitting device described herein to direct and shape the light onto the surgical field.

In any of the embodiments described herein, light may be provided to the waveguide by any number of techniques. An illumination element may be disposed in the handle or adjacent a portion of the waveguide. The illumination element may be a single LED or multiple LEDs. The LED or multiple LEDs may provide white light, or any desired color. For example, when multiple LEDs are used, the LEDs may provide different colors such as red, green, or blue (RGB) and therefore the multiple LEDs may be adjusted to provide a desired color of light that is input into the waveguide. Thus, the waveguide becomes more important since it will mix the different colors of light as the light is transmitted along the length of the waveguide, mixing the different colors of light so that a uniform color light is delivered to the target. Multiple colors may be used to provide varying shades of white colored light, or any other desired color which helps the surgeon or operator visualize and distinguish various objects such as tissue in the surgical field. Filters or coatings may be applied to any of the waveguides to filter specific frequencies of energy out.

Alternatively or in combination, the illumination element may be a fiber optic or fiber bundle in any of the embodiments described herein. For example, a fiber optic may input light to the waveguide from an external source such as a xenon lamp. Light from the external source may be transmitted through the fiber optic or fiber optic bundle through a cable, through the handle, and to the proximal end of the waveguide. The fiber optic or fiber optic bundle may be butted up against the waveguide to provide light to the waveguide and subsequently to a surgical field through the waveguide. A lens or other optical element may be used at the distal end of the fiber optic or fiber bundle to input light to the waveguide with desired optical properties. The light source, for example an external lamp box, may be provided outside the surgical field. Alternatively or in combination, the light source may be a light source in the cable connection. Alternatively or in combination, the light source may be provided in a housing coupled to the cable or to any part of the device.

In any of the embodiments, the waveguide may be made out of a material which has desired optical and mechanical properties. Exemplary materials include acrylic, polycarbonate, cyclo olefin polymer or cylco olefin copolymer. Additionally malleable silicones may be used to form the waveguide so that they may be shaped (plastically deformed) into a desired configuration. Moldable Silicone can also be coupled directly to the energy tip to provide a waveguide coupled to the tip and that flexes with the tip when the tip is bent or otherwise flexed. Manufacturers such as Dow Corning and Nusil produce moldable silicones which may be used to form the waveguide.

Additionally, in any of the embodiments described herein, sensors may be integrated into the waveguide or energy tip. These sensors include but are not limited to image sensors such as CMOS or CCD sensors. Sensors could also be thermal or fiber optic to collect spectroscopic information. Sensors may be disposed or otherwise integrated into the handle.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A light emitting device for illuminating a surgical target, said light emitting device comprising:
a base;
a conductive layer, wherein at least a portion of the conductive layer is coupled to the base, wherein the at least the portion of the conductive layer is positioned atop of the base;
an insulating layer, wherein at least a first portion of the insulating layer is coupled to the conductive layer and a second portion of the insulating layer is coupled to the base, wherein the at least the first portion of the insulating layer is positioned atop of the conductive layer, wherein the at least the second portion of the insulating layer is positioned atop of the base; and
a light emitter coupled to the conductive layer, wherein the light emitter is positioned atop of the conductive layer, wherein a first portion of the light emitter electrically contacts a first portion of the conductive layer and a second portion of the light emitter electrically contacts a second portion of the conductive layer,
wherein the base, the conductive layer, and the insulating layer define one or more holes extending through the base, the conductive layer, and the insulating layer, wherein the one or more holes define:
(i) a first passageway through the base, the first portion of the conductive layer, and the insulating layer, and
(ii) a second passageway through the base, the second portion of the conductive layer, and the insulating layer;
a first conductor element extending entirely through the first passageway and being electrically coupled to the first portion of the conductive layer; and
a second conductor element extending entirely through the second passageway and being electrically coupled to the second portion of the conductive layer.

2. The device of claim 1, wherein the first conductor element is electrically coupled with the first portion of the light emitter via the first portion of the conducting layer, and wherein the second conductor element is electrically coupled with the second portion of the light emitter via the second portion of the conducting layer.

3. The device of claim 1, wherein the one or more holes through the insulating layer are larger in size than the one or more holes through the first portion of the conductive layer and the one or more holes through the second portion of the conductive layer such that the one or more holes through the insulating layer expose (i) a first conductive surface of the first portion of the conductive layer and (ii) a second conductive surface of the second portion of the conductive layer,
  wherein electrical contact between the first conductor element and the first portion of the conductive layer is through the first conductive surface, and
  wherein electrical contact between the second conductor element and the second portion of the conductive layer is through the second conductive surface.

4. The device of claim 1, wherein electrical contact between the first conductor element and the first portion of the conductive layer is through a first conductive, lateral edge of the first portion of the conductive layer, and
  wherein electrical contact between the second conductor element and the second portion of the conductive layer is through a second conductive, lateral edge of the second portion of the conductive layer.

5. The device of claim 1, wherein electrical contact between (i) the first conductor element and the first portion of the conductive layer, and (ii) the second conductor element and the second portion of the conductive layer is through a conductive medium.

6. The device of claim 5, wherein the conductive medium is solder.

7. A light emitting system for illuminating a surgical target, said light emitting system comprising:
  a surgical device with a proximal portion and a distal portion; and
  a light emitting device disposed within the distal portion of the surgical device, the light emitting device comprising:
    a base;
    a conductive layer, wherein at least a portion of the conductive layer is coupled to the base, wherein the at least the portion of the conductive layer is positioned atop of the base;
    an insulating layer, wherein at least a first portion of the insulating layer is coupled to the conductive layer and a second portion of the insulating layer is coupled to the base, wherein the at least the first portion of the insulating layer is positioned atop of the conductive layer, wherein the at least the second portion of the insulating layer is positioned atop of the base; and
    a light emitter coupled to the conductive layer, wherein the light emitter is positioned atop of the conductive layer, wherein a first portion of the light emitter electrically contacts a first portion of the conductive layer and a second portion of the light emitter electrically contacts a second portion of the conductive layer,
  wherein the base, the conductive layer, and the insulating layer define one or more holes extending through the base, the conductive layer, and insulating layer, wherein the one or more holes define:
    (i) a first passageway through the base, the first portion of the conductive layer, and the insulating layer, and
    (ii) a second passageway through the base, the second portion of the conductive layer, and the insulating layer;
  a first conductor element extending entirely through the first passageway and being electrically coupled to the first portion of the conductive layer; and
  a second conductor element extending entirely through the second passageway and being electrically coupled to the second portion of the conductive layer.

8. The system of claim 7, wherein the surgical device comprises a scalpel or an electrode.

9. The system of claim 7, further comprising at least one conductor element, wherein the first conductor element extends through at least one hold extending through the base, the conductive layer, and the insulating layer, and the at least one conductor element is electrically coupled with the first portion of the light emitter via the first portion of the conducting layer, and
  wherein the second conductor element is electrically coupled with the second portion of the light emitter via the second portion of the conducting layer.

10. The system of claim 7, wherein the one or more holes through the insulating layer are larger in size than the one or more holes through the first portion of the conductive layer and the one or more holes through the second portion of the conductive layer such that the one or more holes through the insulating layer expose (i) a first conductive surface of the first portion of the conductive layer and (ii) a second conductive surface of the second portion of the conductive layer,
  wherein electrical contact between the first conductor element and the first portion of the conductive layer is through the first conductive surface, and
  wherein electrical contact between the second conductor element and the second portion of the conductive layer is through the second conductive surface.

11. The system of claim 7, wherein electrical contact between the first conductor element and the first portion of the conductive layer is through a first conductive, lateral edge of the first portion of the conductive layer, and wherein electrical contact between the second conductor element and the second portion of the conductive layer is through a second conductive, lateral edge of the second portion of the conductive layer.

12. The system of claim 7, wherein electrical contact between (i) the first conductor element and the first portion of the conductive layer is through a conductive medium.

13. The system of claim 12, wherein the conductive medium is solder.

14. A method of manufacturing a light emitting device, said method comprising:
  applying solder to a substrate package, wherein the substrate package comprises:
    a base,
    a conductive layer, wherein at least a portion of the conductive layer is coupled to the base, wherein the at least the portion of the conductive layer is positioned atop of the base, and
    an insulating layer, wherein at least a first portion of the insulating layer is coupled to the conductive layer and a second portion of the insulating layer is coupled to the base, wherein the at least the first portion of the insulating layer is positioned atop of the conductive layer, wherein the at least the second portion of the insulating layer is positioned atop of the base, and
    wherein the base, the conductive layer, and the insulating layer define one or more holes extending through the base, the conductive layer, and insulating layer, wherein the one or more holes define (i) a first passageway through the base, the first portion of the conductive layer, and the insulating layer, and (ii) a second passageway through the base, the second portion of the conductive layer, and the insulating layer;

inserting a first conductor element through the first passageway and a second conductor element through the second passageway;

reflowing solder applied to the substrate package a first time;

affixing the substrate package into a machine to remove excess material from the first conductor element and the second conductor element;

removing the excess material from the first conductor element and the second conductor element;

applying a light emitter to the substrate package, wherein a first portion of the light emitter electrically contacts a first portion of the conductive layer and a second portion of the light emitter electrically contacts a second portion of the conductive layer; and after applying the light emitter to the substrate package, reflowing solder applied to the substrate package a second time to fix the light emitter in place and establish electrical contact between (i) the light emitter and the first conductor element via the first portion of the conductive layer, and (ii) the light emitter and the second conductor element via the second portion of the conductive layer.

15. The method of claim 14, wherein the first conductor element and the second conductor element each comprise a pin or wire.

16. The method of claim 14, wherein said affixing the substrate package comprises clamping the substrate package along an overlapping portion of the base into a grinding machine.

17. The method of claim 14, wherein said removing comprises grinding, milling, laser machining such that a top of the first and second conductor elements is about level with the insulating layer.

18. The method of claim 14, wherein reflowing solder the first time comprises placing the substrate package into a reflow oven.

19. The light emitting device of claim 1, wherein the first portion of the light emitter in contact with the first portion of the conductive layer is electrically isolated from the second portion of the light emitter in contact with the second portion of the conductive layer.

20. The light emitting device of claim 1, wherein each of the first conductor element and the second conductor element comprises one conductors selected from a group of conductors consisting of: a wire, a pin, a filament, a fiber, a conductive track, a conductive pad, a conductive substrate, a foil, and a laminate.

21. The light emitting device of claim 1, wherein an entirety of the base comprises one or more materials that are thermally conductive and electrically non-conductive.

22. The light emitting system of claim 7, wherein the first portion of the light emitter in contact with the first portion of the conductive layer is electrically isolated from the second portion of the light emitter in contact with the second portion of the conductive layer.

23. The light emitting system of claim 7, wherein an entirety of the base comprises one or more materials that are thermally conductive and electrically non-conductive.

* * * * *